US009732352B2

(12) United States Patent
Lippman et al.

(10) Patent No.: US 9,732,352 B2
(45) Date of Patent: Aug. 15, 2017

(54) MUTATIONS IN SOLANACEAE PLANTS THAT MODULATE SHOOT ARCHITECTURE AND ENHANCE YIELD-RELATED PHENOTYPES

(71) Applicant: Cold Spring Harbor Laboratory, Cold Spring Harbor, NY (US)

(72) Inventors: Zachary Lippman, North Bellmore, NY (US); Soon-Ju Park, Cold Spring Harbor, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 578 days.

(21) Appl. No.: 13/799,831

(22) Filed: Mar. 13, 2013

(65) Prior Publication Data

US 2014/0143898 A1   May 22, 2014

Related U.S. Application Data

(60) Provisional application No. 61/728,654, filed on Nov. 20, 2012.

(51) Int. Cl.
| | |
|---|---|
| *C12N 15/29* | (2006.01) |
| *C12N 15/82* | (2006.01) |
| *A01H 5/08* | (2006.01) |
| *C07K 14/415* | (2006.01) |
| *A01H 1/02* | (2006.01) |

(52) U.S. Cl.
CPC ............. *C12N 15/827* (2013.01); *A01H 1/02* (2013.01); *A01H 5/08* (2013.01); *C07K 14/415* (2013.01); *C12N 15/8261* (2013.01)

(58) Field of Classification Search
None
See application file for complete search history.

(56) References Cited

U.S. PATENT DOCUMENTS

| | | |
|---|---|---|
| 2010/0212046 A1 | 8/2010 | Heldens |
| 2011/0247093 A1 | 10/2011 | Zamir et al. |
| 2012/0144514 A1 | 6/2012 | de Haan et al. |
| 2015/0284732 A1 | 10/2015 | Lippman et al. |

FOREIGN PATENT DOCUMENTS

WO    WO 2010/041190 A1    4/2010

OTHER PUBLICATIONS

Park et al. (Nature Genetics vol. 46 (12) Dec. 2014, 1337-1342).*
Pnueli et al. (The Plant Cell, vol. 13, 2687-2702, Dec. 2001).*
McCormick (Plant Tissue Culture Manual B6: 1-9, 1991).*
Wigge et al. (Aug. 12, 2005 vol. 309 Science, 1056-1059.*
Taoka et al. (Nature vol. 476, Aug. 18, 2011 332-335).*
Lee et al. (The Plant Cell, vol. 2, 415-425, May 1990).*
Aoki et al. BMC Genomics 2010, 11:210).*
Wigge et al. (Aug. 12, 2005 vol. 309 Science, S1-S8) Supplement.*
Genbank accession ABL84199, dated Dec. 23, 2006.*
Lifschitz et al. (PNAS, Apr. 18, 2006, vol. 103, No. 16, 6398-6403).*
International Search Report and Written Opinion mailed Feb. 24, 2014 for application No. PCT/US2013/070825.
International Preliminary Report on Patentability mailed Jun. 6, 2015 for application No. PCT/US2013/070825.
Genbank Submission; NIH/NCBI, Accession No. NP_0012345345. Lifschitz et al., Nov 30, 2014. 1 page.
Krieger et al., The flowering gene Single Flower Truss drives heterosis for yield in tomato. Nat Genet. May 2010;42(5):459-63. doi:10.1038/ng.550. Epub Mar. 28, 2010.
Lifschitz et al., The tomato FT ortholog triggers systemic signals that regulate growth and flowering and substitute for diverse environmental stimuli. Proc Natl Acad Sci U S A. Apr. 18, 2006;103(16):6398-403. Epub Apr. 10, 2006.
Molinero-Rosales et al., Single Flower Truss regulates the transition and maintenance of flowering in tomato. Planta. Jan. 2004;218(3):427-34. Epub Sep. 23, 2003.
Extended European Search Report for European Application No. EP 13857579 dated May 30, 2016.
Abe et al., FD, a bZIP protein mediating signals from the floral pathway integrator FT at the shoot apex. Science. Aug. 12, 2005;309(5737):1052-6.
Wigge et al., Integration of spatial and temporal information during floral induction in Arabidopsis. Science. Aug. 12, 2005;309(5737):1056-9. Erratum in: Science. Jun. 16, 2006;312(5780):1600.

* cited by examiner

*Primary Examiner* — Shubo (Joe) Zhou
*Assistant Examiner* — Charles Logsdon
(74) *Attorney, Agent, or Firm* — Wolf, Greenfield & Sacks, P.C.

(57) ABSTRACT

Provided herein are genetically-altered Solanaceae plants, compositions related to the Solanaceae plants, and methods of making the Solanaceae plants.

15 Claims, 10 Drawing Sheets

```
 1 CLUSTAL 2.1 multiple sequence alignment
 2
 3
 4 SSP        ATGTGGTCATCAAGCAGTGATAACAGGGGACTCTCTGCTTCTTCTTCTTCATCTTCATCC
 5 ssp-e610   ATGTGGTCATCAAGCAGTGATAACAGGGGACTCTCTGCTTCTTCTTCTTCATCTTCATCC
 6 ssp-e2129  ATGTGGTCATCAAGCAGTGATAACAGGGGACTCTCTGCTTCTTCTTCTTCATCTTCATCC
 7            ************************************************************
 8
 9 SSP        TCATCTCATTCACCATTTTCTCCAAGACTCAAAACAATGGAAGAAGTGTGGAAAGATATT
10 ssp-e610   TCATCTCATTCACCATTTTCTCCAAGACTCAAAACAATGGAAGAAGTGTGGAAAGATATT
11 ssp-e2129  TCATCTCATTCACCATTTTCTCCAAGACTCAAAACAATGGAAGAAGTGTGGAAAGATATT
12            ************************************************************
13
14 SSP        AATCTTTCTTCACTTCAAGATCACACTACGAATTACTCTAGAGATCATCATCATCTTCAT
15 ssp-e610   AATCTTTCTTCACTTCAAGATCACACTACGAATTACTCTAGAGATCATCATCATCTTCAT
16 ssp-e2129  AATCTTTCTTCACTTCAAGATCACACTACGAATTACTCTAGAGATCATCATCATCTTCAT
17            ************************************************************
18
19 SSP        GATCATAATCATCAAGCTGCTAATTTTGGTGGAATGATTTTACAAGATTTTTTGGCAAGG
20 ssp-e610   GATCATAATCATCAAGCTGCTAATTTTGGTGGAATGATTTTACAAGATTTTTTGGCAAGG
21 ssp-e2129  GATCATAATCATCAAGCTGCTAATTTTGGTGGAATGATTTTACAAGATTTTTTGGCAAGG
22            ************************************************************
23
24 SSP        CCTTTTGCTAATGAATCTTCACCAGCAGCAGCAGCAGCAGCAGCCTCCCCTGTTTCAGCT
25 ssp-e610   CCTTTTGCTAATGAATCTTCACCAGCAGCAGCAGCAGCAGCAGCCTCCCCTGTTTCAGCT
26 ssp-e2129  CCTTTTGCTAATGAATCTTCACCAGCAGCAGCAGCAGCAGCAGCCTCCCCTGTTTCAGCT
27            ************************************************************
28
29 SSP        ACAACTATGCTGAATTTGAACTCTGTTCCTGAGCTTCATTTCTTTGATAACCCATTGAGG
30 ssp-e610   ACAACTATGCTGAATTTGAACTCTGTTCCTGAGCTTCATTTCTTTGATAACCCATTGAGG
31 ssp-e2129  ACAACTATGCTGAATTTGAACTCTGTTCCTGAGCTTCATTTCTTTGATAACCCATTGAGG
32            ************************************************************
33
34 SSP        CAAAACTCAATCTTGCACCAACCAAATGCAAGTGGAAGAAAAAGGGTTGTCCCTGAAACA
35 ssp-e610   CAAAACTCAATCTTGCACCAACCAAATGCAAGTGGAAGAAAAAGGGTTGTCCCTGAAACA
36 ssp-e2129  CAAAACTCAATCTTGCACCAACCAAATGCAAGTGGAAGAAAAAGGGTTGTCCCTGAAACA
37            ************************************************************
38
39 SSP        GAAGACAATTCTACAGGGGATAGAAGAAATCAGAGGATGATCAAGAACAGAGAGTCTGCT
40 ssp-e610   GAAGACAATTCTACAGGGGATAGAAGAAATCAGAGGATGATCAAGAACAGAGAGTCTGCT
41 ssp-e2129  GAAGACAATTCTACAGGGGATAGAAGAAATCAGAGGATGATCAAGAACAGAGAGTCTGCT
42            ************************************************************
43
44 SSP        GCTAGATCAAGAGCTAGAAAGCAGGCTTATATGAACGAGTTGGAATCAGAAGTGGCACAT
45 ssp-e610   GCTAGATCAAGAGCTAGAAAGCAGGCTTATATGAACGAGTTGGAATCAGAAGTGGCACAT
```

FIGURE 6A

```
46 ssp-e2129    GCTAGATCAAGAGCTAGAAAGCAGGCTTATATGAACGAGTTGGAATCAGAAGTGGCACAT
47              ************************************************************
48
49 SSP          TTAGTTGAAGAAAATGCAAGGCTCAAGAAGCAGCAGCAACAGTTACGAGTAGATGCAGCT
50 ssp-e610     TTAGTTGAAGAAAATGCAAGGCTCAAGAAGCAGCAGCAACAGTTACGAGTAGATGCAGCT
51 ssp-e2129    TTAGTTGAAGAAAATGCAAGGCTCAAGAAGCAGCAGCAACAGTTACGAGTAGATGCAGCT
52              ************************************************************
53
54 SSP          AATCAAGTTCCCAAAAAGAACACTCTTTATCGGACGTCAACTGCTCCATTTTGA 654
55 ssp-e610     AATCAAGTTCCCAAAAAGAACACTCTTTATCGGACGTCAATTGCTCCATTTTGA 654
56 ssp-e2129    AATCAAGTTCCCAAAAAGAACACTCTTTATCGGACGTCAACTGCTCTATTTTGA 654
57              **************************************** ***** *******
```

FIGURE 6B

```
 1  CLUSTAL 2.1 multiple sequence alignment
 2
 3
 4  SSP         MWSSSSDNRGLSASSSSSSSSSHSPFSPRLKTMEEVWKDINLSSLQDHTTNYSRDHHHLH
 5  ssp-e2129   MWSSSSDNRGLSASSSSSSSSSHSPFSPRLKTMEEVWKDINLSSLQDHTTNYSRDHHHLH
 6  ssp-e610    MWSSSSDNRGLSASSSSSSSSSHSPFSPRLKTMEEVWKDINLSSLQDHTTNYSRDHHHLH
 7              ************************************************************
 8
 9  SSP         DHNHQAANFGGMILQDFLARPFANESSPAAAAAAASPVSATTMLNLNSVPELHFFDNPLR
10  ssp-e2129   DHNHQAANFGGMILQDFLARPFANESSPAAAAAAASPVSATTMLNLNSVPELHFFDNPLR
11  ssp-e610    DHNHQAANFGGMILQDFLARPFANESSPAAAAAAASPVSATTMLNLNSVPELHFFDNPLR
12              ************************************************************
13
14  SSP         QNSILHQPNASGRKRVVPETEDNSTGDRRNQRMIKNRESAARSRARKQAYMNELESEVAH
15  ssp-e2129   QNSILHQPNASGRKRVVPETEDNSTGDRRNQRMIKNRESAARSRARKQAYMNELESEVAH
16  ssp-e610    QNSILHQPNASGRKRVVPETEDNSTGDRRNQRMIKNRESAARSRARKQAYMNELESEVAH
17              ************************************************************
18
19  SSP         LVEENARLKKQQQQLRVDAANQVPKKNTLYRTSTAPF  217
20  ssp-e2129   LVEENARLKKQQQQLRVDAANQVPKKNTLYRTSTALF  217
21  ssp-e610    LVEENARLKKQQQQLRVDAANQVPKKNTLYRTSIAPF  217
22              *********************************  * *
```

MUTATIONS IN SOLANACEAE PLANTS THAT MODULATE SHOOT ARCHITECTURE AND ENHANCE YIELD-RELATED PHENOTYPES

CROSS REFERENCE TO RELATED APPLICATIONS

This application claims the benefit of U.S. Ser. No. 61/728,654, filed on Nov. 20, 2012, which is hereby incorporated by reference to the maximum extent allowable by law.

FEDERALLY SPONSORED RESEARCH OR DEVELOPMENT

This invention was made with government support under grant IOS-1237880 awarded by the National Science Foundation. The government has certain rights in the invention.

BACKGROUND

There are ongoing attempts to enhance yield and quality, as well as life span, of food crops and other plants, such as ornamental plants and trees, in an effort to use resources more efficiently and produce more food, flowers and trees. Additional approaches for doing so are still needed, and one of the primary targets for manipulating plant productivity is the flowering process and its corresponding effects on vegetative and reproductive shoot architecture.

SUMMARY

Described herein are novel genetic variants of Solanaceae plants, e.g., tomato plants, that exhibit modified flowering time and shoot architecture and exhibit higher yield, higher quality products (e.g., fruits) and/or longer lifespan compared to corresponding "wild-type (WT)" Solanaceae plants that have not been genetically altered in the same manner.

In one aspect, the disclosure relates to a genetically-altered semi-determinate Solanaceae plant homozygous for a mutant suppressor of sp1 (ssp1) gene and homozygous for a mutant self pruning (sp) gene. In some embodiments, the mutant ssp1 gene comprises a nucleic acid sequence that encodes a mutant ssp1 protein that comprises a mutant SAP motif. In some embodiments, the mutant ssp1 gene comprises a nucleic acid sequence that encodes a mutant ssp1 protein that comprises a mutant SAP motif with a sequence of SEQ ID NO: 14 or SEQ ID NO: 15. In some embodiments, the mutant ssp1 gene encodes a mutant ssp1 polypeptide comprising the sequence of SEQ ID NO: 5 or SEQ ID NO: 6. In some embodiments, the mutant ssp1 gene comprises a C to T mutation at position 641 of SEQ ID NO: 1, a C to T mutation at position 647 of SEQ ID NO: 1, or a C to T mutation at position 641 and 647 of SEQ ID NO: 1. In some embodiments, the mutant ssp1 gene comprises the nucleic acid sequence of SEQ ID NO: 2 or SEQ ID NO: 3. In some embodiments, the mutant sp gene comprises the nucleic acid sequence of SEQ ID NO: 8. In some embodiments, the genetically-altered semi-determinate Solanaceae plant is a tomato (*Solanum lycopersicum*) plant. In some embodiments, the genetically-altered semi-determinate Solanaceae plant is isogenic. In some embodiments, the genetically-altered semi-determinate Solanaceae plant is inbred. In some embodiments, the genetically-altered semi-determinate Solanaceae plant is a hybrid.

In another aspect, the disclosure relates to a genetically-altered Solanaceae plant heterozygous for a mutant suppressor of sp1 (ssp1) gene and homozygous for a mutant self pruning (sp) gene. In some embodiments, the mutant ssp1 gene comprises a nucleic acid sequence that encodes a mutant ssp1 protein that comprises a mutant SAP motif. In some embodiments, the mutant ssp1 gene comprises a nucleic acid sequence that encodes a mutant ssp1 protein that comprises a mutant SAP motif with a sequence of SEQ ID NO: 14 or SEQ ID NO: 15. In some embodiments, the mutant ssp1 gene encodes a mutant ssp1 polypeptide comprising the sequence of SEQ ID NO: 5 or SEQ ID NO: 6. In some embodiments, the mutant ssp1 gene comprises a C to T mutation at position 641 of SEQ ID NO: 1, a C to T mutation at position 647 of SEQ ID NO: 1, or a C to T mutation at position 641 and 647 of SEQ ID NO: 1. In some embodiments, the mutant ssp1 gene comprises the nucleic acid sequence of SEQ ID NO: 2 or SEQ ID NO: 3. In some embodiments, the mutant sp gene comprises the nucleic acid sequence of SEQ ID NO: 8. In some embodiments, the genetically-altered Solanaceae plant is a tomato (*Solanum lycopersicum*) plant. In some embodiments, the genetically-altered Solanaceae plant is isogenic. In some embodiments, the genetically-altered Solanaceae plant is inbred. In some embodiments, the genetically-altered semi-determinate Solanaceae plant is a hybrid.

In another aspect, the disclosure relates to a genetically-altered Solanaceae plant homozygous for a mutant suppressor of sp1 (ssp1) gene. In some embodiments, the mutant ssp1 gene comprises a nucleic acid sequence that encodes a mutant ssp1 protein that comprises a mutant SAP motif. In some embodiments, the mutant ssp1 gene comprises a nucleic acid sequence that encodes a mutant ssp1 protein that comprises a mutant SAP motif with a sequence of SEQ ID NO: 14 or SEQ ID NO: 15. In some embodiments, the mutant ssp1 gene encodes a mutant ssp1 polypeptide comprising the sequence of SEQ ID NO: 5 or SEQ ID NO: 6. In some embodiments, the mutant ssp1 gene comprises a C to T mutation at position 641 of SEQ ID NO: 1, a C to T mutation at position 647 of SEQ ID NO: 1, or a C to T mutation at position 641 and 647 of SEQ ID NO: 1. In some embodiments, the mutant ssp1 gene comprises the nucleic acid sequence of SEQ ID NO: 2 or SEQ ID NO: 3. In some embodiments, the mutant sp gene comprises the nucleic acid sequence of SEQ ID NO: 8. In some embodiments, the genetically-altered Solanaceae plant is a tomato (*Solanum lycopersicum*) plant. In some embodiments, the genetically-altered Solanaceae plant is isogenic. In some embodiments, the genetically-altered Solanaceae plant is inbred. In some embodiments, the genetically-altered semi-determinate Solanaceae plant is a hybrid. In some embodiments, the genetically-altered Solanaceae plant is homozygous for a wild-type SELF PRUNING (SP) gene.

In another aspect, the disclosure relates to a seed for producing a genetically-altered semi-determinate Solanaceae plant as described herein, e.g., a genetically-altered semi-determinate Solanaceae plant homozygous for a mutant suppressor of sp1 (ssp1) gene and homozygous for a mutant self pruning (sp) gene. In some embodiments, the mutant ssp1 gene comprises a nucleic acid sequence that encodes a mutant ssp1 protein that comprises a mutant SAP motif. In some embodiments, the mutant ssp1 gene comprises a nucleic acid sequence that encodes a mutant ssp1 protein that comprises a mutant SAP motif with a sequence of SEQ ID NO: 14 or SEQ ID NO: 15. In some embodiments, the mutant ssp1 gene encodes a mutant ssp1 polypeptide comprising the sequence of SEQ ID NO: 5 or SEQ ID NO: 6. In some embodiments, the mutant ssp1 gene comprises a C to T mutation at position 641 of SEQ ID NO: 1, a C to T mutation at position 647 of SEQ ID NO: 1, or a C to T mutation at position 641 and 647 of SEQ ID NO: 1. In some embodiments, the mutant ssp1 gene comprises the nucleic acid sequence of SEQ ID NO: 2 or SEQ ID NO: 3. In some embodiments, the mutant sp gene comprises the nucleic acid sequence of SEQ ID NO: 8.

In yet another aspect, the disclosure relates to methods of producing a genetically-altered semi-determinate Solanaceae plant. In some embodiments, the method comprises:

(a) introducing a mutant ssp1 gene into a Solanaceae plant containing a mutant sp gene, thereby producing a genetically-altered Solanaceae plant containing a mutant ssp1 gene and a mutant sp gene; and (b) self-crossing the genetically-altered Solanaceae plant produced in (a) or crossing two genetically-altered Solanaceae plants produced in (a) under conditions appropriate for producing a genetically-altered Solanaceae plant homozygous for the mutant ssp1 gene and the mutant sp gene, thereby producing a genetically-altered Solanaceae plant that is semi-determinate. In some embodiments, the method of producing a genetically-altered semi-determinate Solanaceae plant comprises:

(a) introducing a mutant ssp1 gene into an Solanaceae plant part containing a mutant sp gene, thereby producing a genetically-altered Solanaceae plant part containing the mutant ssp1 gene and the mutant sp gene;

(b) maintaining the genetically-altered Solanaceae plant part containing a mutant ssp1 and a mutant sp gene produced in (a) under conditions and for sufficient time for production of a genetically-altered Solanaceae plant containing the mutant ssp1 gene and the mutant sp gene from the plant part, thereby producing a genetically-altered Solanaceae plant containing the mutant ssp1 gene and the mutant sp gene;

(c) self-crossing the genetically-altered Solanaceae plant produced in (b) or crossing two genetically-altered Solanaceae plants produced in (b) under conditions appropriate for producing a genetically-altered Solanaceae plant homozygous for the mutant ssp1 gene and the mutant sp gene, thereby producing a genetically-altered plant Solanaceae that is semi-determinate. In some embodiments, the mutant ssp1 gene comprises a nucleic acid sequence that encodes a mutant ssp1 protein that comprises a mutant SAP motif. In some embodiments, the mutant ssp1 gene comprises a nucleic acid sequence that encodes a mutant ssp1 protein that comprises a mutant SAP motif with a sequence of SEQ ID NO: 14 or SEQ ID NO: 15. In some embodiments, the mutant ssp1 gene encodes a mutant ssp1 polypeptide comprising the sequence of SEQ ID NO: 5 or SEQ ID NO: 6. In some embodiments, the mutant ssp1 gene comprises a C to T mutation at position 641 of SEQ ID NO: 1, a C to T mutation at position 647 of SEQ ID NO: 1, or a C to T mutation at position 641 and 647 of SEQ ID NO: 1. In some embodiments, the mutant ssp1 gene comprises the nucleic acid sequence of SEQ ID NO: 2 or SEQ ID NO: 3. In some embodiments, the mutant sp gene comprises the nucleic acid sequence of SEQ ID NO: 8. In some embodiments, the mutant ssp1 gene is introduced into a plant or a plant part by a method selected from the group consisting of: *Agrobacterium*-mediated recombination, viral-vector mediated recombination, microinjection, gene gun bombardment/biolistic particle delivery, nuclease mediated recombination, and electroporation. In some embodiments, the Solanaceae plant is a tomato (*Solanum lycopersicum*) plant. In some embodiments, the Solanaceae plant is inbred. In some embodiments, the genetically-altered semi-determinate Solanaceae plant is a hybrid. In another aspect, the disclosure relates to a genetically-altered semi-determinate Solanaceae plant produced by the methods herein.

Other aspects of the disclosure relate to isolated polynucleotides or isolated polypeptides. In some embodiments, the isolated polynucleotide encodes a mutant ssp1 protein having the amino acid sequence of SEQ ID NO: 5 or SEQ ID NO: 6. In some embodiments, the isolated polynucleotide comprises the nucleic acid sequence of SEQ ID NO: 2 or SEQ ID NO: 3.

BRIEF DESCRIPTION OF THE DRAWINGS

FIG. 4A shows the numbers of leaves produced by PSM in M82ID, M82D and ssp-2129 and ssp-610. FIG. 4B shows the numbers of flowers per inflorescence in M82ID, M82D and ssp-2129 and ssp-610. FIG. 4C shows the numbers of leaves from each SYM shoot in M82ID, M82D and ssp-2129 and ssp-610. Numbers in parentheses indicate mean values. ID, indeterminate SYM growth; D, determinate SYM growth; SD, semi-determinate SYM growth. ** $P<0.01$, * $P<0.05$, students t-test against M82D.

FIGS. 6A and 6B is a ClustalW analysis of the nucleotide sequence of the wild-type SSP/gene (SEQ ID NO: 16) and the two mutant alleles e610 and e2129 (SEQ ID NOs: 17 and 18, respectively).

FIG. 7 is a ClustalW analysis of the amino acid sequence of the wild-type SSP/gene (SEQ ID NO: 19) and the two mutant alleles e2129 and e610 (SEQ ID NOs: 20 and 21, respectively).

SEQUENCES

SEQ ID NO: 1 is the nucleotide sequence of wild-type tomato SSP1.
SEQ ID NO: 2 is the nucleotide sequence of ssp-2129, a mutant allele of SSP1.
SEQ ID NO: 3 is the nucleotide sequence of ssp-610, a mutant allele of SSP1.
SEQ ID NO: 4 is the amino acid sequence of wild-type tomato SSP1 protein.
SEQ ID NO: 5 is the amino acid sequence of ssp-2129 mutant protein.
SEQ ID NO: 6 is the amino acid sequence of ssp-610 mutant protein.
SEQ ID NO: 7 is the nucleotide sequence of wild-type tomato SP gene
SEQ ID NO: 8 is the nucleotide sequence of a mutant sp gene.
SEQ ID NO: 9 is the amino acid sequence of wild-type SP protein
SEQ ID NO: 10 is the amino acid sequence of mutant sp protein
SEQ ID NO: 11 is the amino acid sequence of the SAP motif of the tomato SSP1 protein
SEQ ID NO: 12 is the nucleotide sequence of ssp-2129 that encodes the mutant SAP motif of ssp-2129 protein
SEQ ID NO: 13 is the nucleotide sequence of ssp-610 that encodes the mutant SAP motif of ssp-610 protein
SEQ ID NO: 14 is the amino acid sequence of the mutant SAP motif of ssp-2129 protein
SEQ ID NO: 15 is the amino acid sequence of the mutant SAP motif of ssp-610 protein

DETAILED DESCRIPTION

Figure 1:
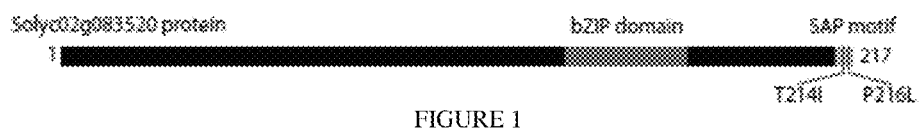
FIG. 1 shows the SSP1 protein. The bZIP domain and SAP motif are indicated. Mutations in the SAP motif are indicated.

Described herein are semi-determinate (SD) Solanaceae plants, e.g., a tomato plant (*Solanum lycopersicum*), that comprise a mutant flowering gene known from the model plant *Arabidopsis thaliana* as FLOWERING LOCUS D (FD) gene, which is herein referred to by the tomato FD gene designation of "SUPPRESSOR OF SP1" (SSP1). The SSP1 encodes a bZIP transcription factor that physically interacts with the florigen hormone, FLOWERING LOCUS T (FT, known as SFT in tomato), to induce the flowering transition and flower production. SSP1 has two domains, the bZIP domain and the SAP motif (FIG. 1). The bZIP domain contains a basic leucine zipper capable of interacting with DNA. The SAP motif, "RTSTAPF" (SEQ ID NO: 11), is found in the C-terminus of SSP1 from amino acid position 211 to 217 in SEQ ID NO: 4. The SAP motif is similar to a conventional 14-3-3 recognition motif.

In some embodiments, the mutant ssp1 gene comprises, for example, a nucleic acid (e.g., DNA) having the sequence of SEQ ID NO: 2; a portion of SEQ ID NO: 2 that exhibits substantially the same activity as a nucleic acid (e.g., DNA) having the sequence of SEQ ID NO: 2; a nucleic acid (e.g., DNA) having the sequence of positions 631 to 651 of SEQ ID NO: 2 (CGGACGTCAACTGCTCTATTT, SEQ ID NO: 12); an orthologue or homologue of the nucleic acid having the sequence of SEQ ID NO: 2; an orthologue or homologue of the nucleic acid sequence of positions 631 to 651 of SEQ ID NO: 2; a nucleic acid (e.g., DNA) having the sequence of SEQ ID NO: 3; a portion of SEQ ID NO: 3 that exhibits substantially the same activity as a nucleic acid (e.g., DNA) having the sequence of SEQ ID NO: 3; a nucleic acid (e.g., DNA) having the sequence of positions 631 to 651 of SEQ ID NO: 3 (CGGACGTCAATTGCTCCATTT, SEQ ID NO: 13); an orthologue or homologue of the nucleic acid having the sequence of SEQ ID NO: 3; or an orthologue or homologue of the nucleic acid sequence of positions 631 to 651 of SEQ ID NO: 3. In some embodiments, the mutant ssp1 gene comprises a C to T mutation at position 641 of SEQ ID NO: 1, a C to T mutation at position 647 of SEQ ID NO: 1, or a C to T mutation at position 641 and position 647 of SEQ ID NO: 1. In some embodiments, the mutant ssp1 gene comprises a nucleotide sequence that encodes a polypeptide of SEQ ID NOs: 5 or 6 or a nucleotide sequence that encodes a polypeptide that comprises SEQ ID NOs: 14 or 15. In some embodiments, the mutant ssp1 gene comprises a nucleic acid sequence that encodes a mutant ssp1 protein that comprises at least one mutation in a SAP motif, wherein the at least one mutation alters flowering time and shoot architecture of the Solanaceae plant, e.g., by conferring semi-determinacy. In some embodiments, the SAP motif with the at least one mutation has the amino acid sequence SEQ ID NO: 14 or SEQ ID NO: 15. In some embodiments, the mutant ssp1 gene comprises a nucleic acid sequence that encodes a mutant ssp1 protein that comprises at least one mutation in a SAP motif or in the two amino acids flanking the N-terminal position of the SAP motif and the one amino acid flanking the C-terminal position of the SAP motif, which includes the phosphorylation site for Ca-dependent protein kinases (CDPKs), wherein the at least one mutation alters flowering time and shoot architecture of the Solanaceae plant, e.g., by conferring semi-determinacy.

In some embodiments, the semi-determinate (SD) Solanaceae plant, e.g., a tomato plant, comprises a mutant spp1 polypeptide (e.g., a mutant ssp1 protein) encoded by a mutant ssp1 gene. In some embodiments, the mutant ssp1 polypeptide comprises the sequence of SEQ ID NO: 5; a portion of SEQ ID NO: 5 that exhibits substantially the same activity as a polypeptide (e.g., a protein) having the sequence of SEQ ID NO: 5; the amino acid sequence of positions 211 to 217 in SEQ ID NO: 5 (RTSTALF, SEQ ID NO: 14); an orthologue or homologue of the polypeptide having the sequence of SEQ ID NO: 5; an orthologue or homologue of the amino acid sequence of positions 211 to 217 in SEQ ID NO: 5 (RTSTALF, SEQ ID NO: 14); a polypeptide (e.g., a protein) having the sequence of SEQ ID NO: 6; a portion of SEQ ID NO: 6 that exhibits substantially the same activity as a polypeptide (e.g., a protein) having the sequence of SEQ ID NO: 6; the sequence of positions 211 to 217 in SEQ ID NO: 6 (RTSIAPF, SEQ ID NO: 15); an orthologue or homologue of the polypeptide having the sequence of SEQ ID NO: 6; or an orthologue or homologue of the polypeptide sequence of positions 211 to 217 in SEQ ID NO: 6 (RTSIAPF, SEQ ID NO: 15). In some embodiments, the polypeptide comprises a Thr to Ile mutation at position 214 of SEQ ID NO: 4 or a Pro to Leu mutation at position 216 of SEQ ID NO: 4, or a Thr to Ile mutation at position 214 and a Pro to Leu mutation at position 216 of SEQ ID NO: 4. In some embodiments, the mutant ssp1 polypeptide comprises an amino acid sequence with at least one mutation in a SAP motif, wherein the at least one mutation alters flowering time and shoot architecture of the Solanaceae plant, e.g., by conferring semi-determinacy. In some embodiments, the SAP motif with the at least one mutation has the amino acid sequence SEQ ID NO: 14 or SEQ ID NO: 15. In some embodiments, the mutant ssp1 polypeptide comprises an amino acid sequence with at least one mutation in a SAP motif or in the two amino acids flanking the N-terminal position of the SAP motif and the one amino acid flanking the C-terminal position of the SAP motif, which includes the phosphorylation site for Ca-dependent protein kinases (CDPKs), wherein the at least one mutation alters flowering time and shoot architecture of the Solanaceae plant, e.g., by conferring semi-determinacy.

Flowering time and shoot architecture can be manipulated in a wide variety of types of Solanaceae plants that comprise a mutant ssp1 gene or two mutant genes—a mutant ssp1 gene and a mutant terminal flower1 (tfl1) gene. TFL1 is the antagonist of florigen (FT) and is herein referred to by the tomato TFL1 gene designation of SELF-PRUNING (SP). The mutant ssp1 gene can comprise, for example, any of the nucleic acids described herein. In specific embodiments, the mutant ssp1 gene is present with a mutant self-pruning (sp) gene in a double mutant background and the mutant sp gene (Pnueli et al. Development. 1998; 125(11):1979-89) comprises, for example, a nucleic acid (e.g., DNA) having the sequence of SEQ ID NO: 8; a portion of SEQ ID NO: 8 that exhibits substantially the same activity as a nucleic acid (e.g., DNA) having the sequence of SEQ ID NO: 8; or an orthologue or homologue of the nucleic acid having the sequence of SEQ ID NO: 8. In some embodiments, the mutant sp gene comprises a C to T mutation at position 227 of SEQ ID NO: 7. In some embodiments, the mutant sp gene comprises a nucleotide sequence with at least one mutation that reduces the activity of a sp protein encoded by the mutant sp gene. In some embodiments, the mutant sp gene comprises a nucleotide sequence that encodes a polypeptide of SEQ ID NO: 10. In some embodiments, the SD Solanaceae plant comprises a mutant sp polypeptide (e.g., a protein) encoded by a mutant sp gene. In some embodiments, the mutant sp polypeptide comprises, for example, the sequence of SEQ ID NO: 10; a portion of SEQ ID NO: 10 that exhibits substantially the same activity as a polypeptide (e.g., a protein) having the sequence of SEQ ID NO: 10; or an orthologue or homologue of the polypeptide having the sequence of SEQ ID NO: 10. In some embodiments, the mutant sp polypeptide comprises a Pro to Leu mutation at position 76 of SEQ ID NO: 9. In some embodiments, the mutant sp polypeptide comprises at least one mutation that reduces (partially or completely) the activity of the sp polypeptide. In some embodiments, the mutant sp polypeptide comprises at least one mutation that reduces the activity of the sp polypeptide, wherein the reduced (partially or completely) activity of the sp polypeptide can confer determinacy.

The Solanaceae plant can be, for example, inbred, isogenic or hybrid, as long as the plant comprises a mutant ssp1 gene or a mutant ssp1 gene and a mutant sp gene. Plants in the Solanaceae family include, e.g., tomato, potato, eggplant, petunia, tobacco, and pepper. In some embodiments, the Solanaceae plant is a tomato plant. In some embodiments, the Solanaceae plant comprises one wild-type copy of the SSP1 gene and one mutant copy of the ssp1 gene as described herein (is heterozygous for the mutant ssp1 gene). In some embodiments, the Solanaceae plant comprises two copies of a mutant ssp1 gene as described herein (is homozygous for the mutant ssp1 gene). In some embodiments, the Solanaceae plant comprises a first mutant ssp1 gene as described herein and a second mutant ssp1 gene as described herein, wherein the first mutant ssp1 gene and the second mutant ssp1 gene are different (e.g., the first mutant ssp1 gene comprises SEQ ID NO: 2 and the second mutant ssp1 gene comprises SEQ ID NO: 3). In some embodiments, the Solanaceae plant comprises one copy of a mutant ssp1 gene as described herein and one copy of a mutant sp gene as described herein (is heterozygous for the mutant ssp1 gene and heterozygous for mutant sp gene). In some embodiments, the Solanaceae plant comprises one copy of a mutant ssp1 gene as described herein and two copies of a mutant sp gene as described herein (is heterozygous for the mutant ssp1 gene and homozygous for the mutant sp gene). In some embodiments, the Solanaceae plant comprises two copies of a mutant ssp1 gene as described herein and two copies of a mutant sp gene as described herein (is homozygous for the mutant ssp1 gene and homozygous for the mutant sp gene). In some embodiments, any of the Solanaceae plants described above have an altered flowering time and shoot architecture compared to a wild-type Solanaceae plant, to a determinate Solanaceae plant (e.g., a Solanaceae plant comprising a mutant sp gene), or to both a wild-type Solanaceae plant and a determinate Solanaceae plant. In some embodiments, any of the Solanaceae plants described above have a higher yield and/or longer lifespan than a wild-type Solanaceae plant. In some embodiments, a Solanaceae plant comprising two copies of a mutant ssp1 gene as described herein and two copies of a wild-type SP gene as described herein has altered flowering time compared to a wild-type Solanaceae plant. In some embodiments, a Solanaceae plant comprising one copy of a mutant ssp1 gene as described herein and two copies of a mutant sp gene as described herein is semi-determinate. In some embodiments, a Solanaceae plant comprising two copies of a mutant ssp1 gene as described herein and two copies of a mutant sp gene as described herein is semi-determinate.

Isolated polynucleotides are also described herein, including wild-type and mutant alleles of the SSP1 gene, and specifically, two mutant alleles designated herein as ssp-2129 and ssp-610. Isolated polynucleotides can comprise, for example, a nucleic acid (e.g., DNA) having the sequence of SEQ ID NO: 2; a portion of SEQ ID NO: 2 that exhibits substantially the same activity as a nucleic acid (e.g., DNA) having the sequence of SEQ ID NO: 2; a nucleic acid (e.g., DNA) having the sequence of positions 631 to 651 of SEQ ID NO: 2 (CGGACGTCAACTGCTCTATTT, SEQ ID NO: 12); an orthologue or homologue of the nucleic acid having the sequence of SEQ ID NO: 2; an orthologue or homologue of the nucleic acid sequence of positions 631 to 651 of SEQ ID NO: 2; a nucleic acid (e.g., DNA) having the sequence of SEQ ID NO: 3; a portion of SEQ ID NO: 3 that exhibits substantially the same activity as a nucleic acid (e.g., DNA) having the sequence of SEQ ID NO: 3; a nucleic acid (e.g., DNA) having the sequence of positions 631 to 651 of SEQ ID NO: 3 (CGGACGTCAATTGCTCCATTT, SEQ ID NO: 13); an orthologue or homologue of the nucleic acid having the sequence of SEQ ID NO: 3; or an orthologue or homologue of the nucleic acid sequence of positions 631 to 651 of SEQ ID NO: 3. In some embodiments, the isolated polynucleotide comprises a mutant ssp1 gene that includes a C to T mutation at position 641 of SEQ ID NO: 1, a C to T mutation at position 647 of SEQ ID NO: 1, or a C to T mutation at position 641 and position 647 of SEQ ID NO: 1. In some embodiments, the isolated polynucleotide comprises a nucleotide sequence that encodes the polypeptide of SEQ ID NOs: 5 or 6 or a nucleotide sequence that encodes a polypeptide that comprises SEQ ID NOs: 14 or 15. In some embodiments, the isolated polynucleotide comprises a nucleic acid sequence that encodes a mutant ssp1 protein that comprises at least one mutation in a SAP motif, wherein the at least one mutation alters flowering time and shoot architecture of the Solanaceae plant, e.g., by conferring semi-determinacy. In some embodiments, the SAP motif with the at least one mutation has the amino acid sequence SEQ ID NO: 14 or SEQ ID NO: 15. In some embodiments, the isolated polynucleotide comprises a nucleic acid sequence that encodes a mutant ssp1 protein that comprises at least one mutation in the SAP motif or in the two amino acids flanking the N-terminal position of the SAP motif and the one amino acid flanking the C-terminal position of the SAP motif, which includes the phosphorylation site for Ca-dependent protein kinases (CDPKs), wherein the at least one mutation alters flowering time and shoot architecture of the Solanaceae plant, e.g., by conferring semi-determinacy. Such isolated polynucleotides can be used, for example, in methods of producing genetically-altered semi-determinate plants.

Isolated polypeptides (e.g., proteins) are also described herein, including wild-type and mutant ssp1 polypeptides, and specifically, the polypeptides encoded by the two mutant alleles ssp-2129 and ssp-610. In some embodiments, the isolated polypeptide comprises, for example, the sequence of SEQ ID NO: 5; a portion of SEQ ID NO: 5 that exhibits substantially the same activity as a polypeptide (e.g., a protein) having the sequence of SEQ ID NO: 5; the amino acid sequence of positions 211 to 217 in SEQ ID NO: 5 (RTSTALF, SEQ ID NO: 14); an orthologue or homologue of the polypeptide having the sequence of SEQ ID NO: 5; an orthologue or homologue of the amino acid sequence of positions 211 to 217 in SEQ ID NO: 5 (RTSTALF, SEQ ID NO: 14); a polypeptide (e.g., a protein) having the sequence of SEQ ID NO: 6; a portion of SEQ ID NO: 6 that exhibits substantially the same activity as a polypeptide (e.g., a protein) having the sequence of SEQ ID NO: 6; the sequence of positions 211 to 217 in SEQ ID NO: 6 (RTSIAPF, SEQ ID NO: 15); an orthologue or homologue of the polypeptide having the sequence of SEQ ID NO: 6; or an orthologue or homologue of the polypeptide sequence of positions 211 to 217 in SEQ ID NO: 6 (RTSIAPF, SEQ ID NO: 15). In some embodiments, the isolated polypeptide comprises a Thr to Ile mutation at position 214 of SEQ ID NO: 4 or a Pro to Leu mutation at position 216 of SEQ ID NO: 4, or a Thr to Ile mutation at position 214 and a Pro to Leu mutation at position 216 of SEQ ID NO: 4. In some embodiments, the isolated polypeptide comprises a mutant ssp1 protein comprising an amino acid sequence with at least one mutation in a SAP motif, wherein the at least one mutation alters flowering time and shoot architecture of the Solanaceae plant, e.g., by conferring semi-determinacy. In some embodiments, the SAP motif with the at least one mutation has the amino acid sequence SEQ ID NO: 14 or SEQ ID NO: 15. In some embodiments, the isolated polypeptide comprises a mutant ssp1 protein comprising an amino acid sequence with at least one mutation in a SAP motif or in the two amino acids flanking the N-terminal position of the SAP motif and the one amino acid flanking the C-terminal position of the SAP motif, which includes the phosphorylation site for Ca-dependent protein kinases (CDPKs), wherein the at least one mutation alters flowering time and shoot architecture of the Solanaceae plant, e.g., by conferring semi-determinacy. Such isolated polypeptides can be used, for example, in methods of producing genetically-altered semi-determinate plants.

Also described herein are methods of modifying flowering time and shoot architecture in a Solanaceae plant, such as tomato, particularly suppressing sympodial shoot termination, which results in increased number of leaves in a Solanaceae plant compared to corresponding determinate (e.g., a sp mutant) plants maintained under the same conditions, but fewer leaves compared to indeterminate wild-type plants (see, e.g., FIGS. 2 and 4). Methods described are methods of producing a genetically-altered Solanaceae semi-determinate (SD) plant or producing a Solanaceae plant with an altered flowering time and shoot architecture compared to a wild-type Solanaceae plant. In one embodiment, a method of producing a semi-determinate genetically-altered Solanaceae plant comprises: (a) introducing a mutant ssp1 gene into a Solanaceae plant that comprises a mutant sp gene or producing a mutant ssp1 gene in a Solanaceae plant that comprises a mutant sp gene, thereby producing a genetically-altered plant that comprises the mutant ssp1 gene and the mutant sp gene; (b) self-crossing the genetically-altered Solanaceae plant produced in (a) or crossing two genetically-altered Solanaceae plants produced in (a) under conditions appropriate for producing a genetically-altered Solanaceae plant homozygous for the mutant ssp1 gene and homozygous for the mutant sp gene, thereby producing a genetically-altered Solanaceae plant that is homozygous for the mutant ssp1 gene and the mutant sp gene and is semi-determinate. In another embodiment, a method of producing a genetically-altered Solanaceae plant with an altered flowering time and shoot architecture compared to a wild-type Solanaceae plant comprises: (a) introducing a mutant ssp1 gene into a Solanaceae plant that comprises a mutant sp gene or producing a mutant ssp1 gene in a Solanaceae plant that comprises a mutant sp gene, thereby producing a genetically-altered plant that comprises the mutant ssp1 gene and the mutant sp gene; (b) self-crossing the genetically-altered Solanaceae plant produced in (a) or crossing two genetically-altered Solanaceae plants produced in (a) under conditions appropriate for producing a genetically-altered Solanaceae plant heterozygous for the mutant ssp1 gene and homozygous for the mutant sp gene, thereby producing a genetically-altered Solanaceae plant that is heterozygous for the mutant ssp1 gene and homozygous for the mutant sp gene and has an altered flowering time and shoot architecture compared to a wild-type Solanaceae plant.

In specific embodiments of the method, the mutant ssp1 gene comprises, for example, a nucleic acid (e.g., DNA) having the sequence of SEQ ID NO: 2; a portion of SEQ ID NO: 2 that exhibits substantially the same activity as a nucleic acid (e.g., DNA) having the sequence of SEQ ID NO: 2; a nucleic acid (e.g., DNA) having the sequence of positions 631 to 651 of SEQ ID NO: 2 (CGGACGTCAACTGCTCTATTT, SEQ ID NO: 12); an orthologue or homologue of the nucleic acid having the sequence of SEQ ID NO: 2; an orthologue or homologue of the nucleic acid sequence of positions 631 to 651 of SEQ ID NO: 2; a nucleic acid (e.g., DNA) having the sequence of SEQ ID NO: 3; a portion of SEQ ID NO: 3 that exhibits substantially the same activity as a nucleic acid (e.g., DNA) having the sequence of SEQ ID NO: 3; a nucleic acid (e.g., DNA) having the sequence of positions 631 to 651 of SEQ ID NO: 3 (CGGACGTCAATTGCTCCATTT, SEQ ID NO: 13); an orthologue or homologue of the nucleic acid having the sequence of SEQ ID NO: 3; or an orthologue or homologue of the nucleic acid sequence of positions 631 to 651 of SEQ ID NO: 3. In some embodiments, the mutant ssp1 gene comprises a C to T mutation at position 641 of SEQ ID NO: 1, a C to T mutation at position 647 of SEQ ID NO: 1, or a C to T mutation at position 641 and position 647 of SEQ ID NO: 1. In some embodiments, the mutant ssp1 gene comprises a nucleotide sequence that encodes a polypeptide of SEQ ID NOs: 5 or 6 or a nucleotide sequence that encodes a polypeptide that comprises SEQ ID NOs: 14 or 15. In some embodiments, the mutant ssp1 gene comprises a nucleic acid sequence that encodes a mutant ssp1 protein that comprises at least one mutation in a SAP motif, wherein the at least one mutation alters flowering time and shoot architecture of the Solanaceae plant, e.g., by conferring semi-determinacy. In some embodiments, the SAP motif with the at least one mutation has the amino acid sequence SEQ ID NO: 14 or SEQ ID NO: 15. In some embodiments, the mutant ssp1 gene comprises a nucleic acid sequence that encodes a mutant ssp1 protein that comprises at least one mutation in a SAP motif or in the two amino acids flanking the N-terminal position of the SAP motif and the one amino acid flanking the C-terminal position of the SAP motif, which includes the phosphorylation site for Ca-dependent protein kinases (CDPKs), wherein the at least one mutation alters flowering time and shoot architecture of the Solanaceae plant, e.g., by conferring semi-determinacy.

In specific embodiments, the sp mutant gene comprises, for example, a nucleic acid (e.g., DNA) having the sequence of SEQ ID NO: 8; a portion of SEQ ID NO: 8 that exhibits substantially the same activity as a nucleic acid (e.g., DNA) having the sequence of SEQ ID NO: 8; or an orthologue or homologue of the nucleic acid having the sequence of SEQ ID NO: 8. In some embodiments, the mutant sp gene comprises a C to T mutation at position 227 of SEQ ID NO: 7. In some embodiments, the mutant sp gene comprises at least one mutation that reduces the activity of a sp protein encoded by the mutant sp gene. In some embodiments, the mutant sp gene comprises at least one mutation that reduces (partially or completely) the activity of a sp protein encoded by the mutant sp gene, wherein the reduced activity can confer determinacy. In some embodiments, the mutant sp gene comprises a nucleotide sequence that encodes a polypeptide of SEQ ID NO: 10.

Alternatively, a method of producing a genetically-altered semi-determinate Solanaceae plant comprises: (a) introducing a mutant ssp1 gene into a Solanaceae plant part (e.g., a leaf or seed) that comprises a mutant sp gene or producing a mutant ssp1 gene in a Solanaceae plant part (e.g., a leaf or seed) that comprises a mutant sp gene, thereby producing a genetically-altered Solanaceae plant part that contains the mutant ssp1 gene and the mutant sp gene; (b) maintaining the genetically-altered Solanaceae plant part containing the mutant ssp1 gene produced in (a) under conditions and for sufficient time for production of a genetically-altered Solanaceae plant containing the mutant ssp1 gene and the mutant sp gene from the plant part, thereby producing a genetically-altered Solanaceae plant that contains the mutant ssp1 gene and a mutant sp gene; (c) self-crossing the genetically-altered Solanaceae plant produced in (b) or crossing two genetically-altered Solanaceae plants produced in (b) under conditions appropriate for producing a genetically-altered Solanaceae plant homozygous for the mutant ssp1 gene and the mutant sp gene, thereby producing a genetically-altered Solanaceae plant that is homozygous for the mutant ssp1 gene and the mutant sp gene and is semi-determinate. In another embodiment, a method of producing a genetically-altered Solanaceae plant with an altered flowering time and shoot architecture compared to a wild-type Solanaceae plant comprises: (a) introducing a mutant ssp1 gene into a Solanaceae plant part (e.g., a leaf or seed) that comprises a mutant sp gene or producing a mutant ssp1 gene in a Solanaceae plant part (e.g., a leaf or seed) that comprises a mutant sp gene, thereby producing a genetically-altered Solanaceae plant part that contains the mutant ssp1 gene and the mutant sp gene; (b) maintaining the genetically-altered Solanaceae plant part containing the mutant ssp1 gene produced in (a) under conditions and for sufficient time for production of a genetically-altered Solanaceae plant containing the mutant ssp1 gene and the mutant sp gene from the plant part, thereby producing a genetically-altered Solanaceae plant that contains the mutant ssp1 gene and a mutant sp gene; (c) self-crossing the genetically-altered Solanaceae plant produced in (b) or crossing two genetically-altered Solanaceae plants produced in (b) under conditions appropriate for producing a genetically-altered Solanaceae plant heterozygous for the mutant ssp1 gene and homozygous for the mutant sp gene, thereby producing a genetically-altered Solanaceae plant that is heterozygous for the mutant ssp1 gene and homozygous for the sp gene and has an altered flowering time and shoot architecture compared to a wild-type Solanaceae plant. The mutant ssp1 gene and the mutant sp gene can be as described above.

In any of the methods described herein, the mutant ssp1 gene can be introduced into a Solanaceae plant or a plant part or produced in a Solanaceae plant or plant part by a method known to those of skill in the art, such as *Agrobacterium*-mediated recombination, viral-vector mediated recombination, microinjection, gene gun bombardment/biolistic particle delivery, electroporation, mutagenesis (e.g., by ethyl methanesulfonate or fast neutron irradiation), TILLING (Targeting Induced Local Lesions in Genomes), and nuclease mediated recombination (e.g., use of custom-made restriction enzymes for targeting mutagenesis by gene replacement, see, e.g., TALEN endonucleases: Nucleic Acids Res. 2011 July; 39(12):e82. Efficient design and assembly of custom TALEN and other TAL effector-based constructs for DNA targeting. Cermak T, Doyle E L, Christian M, Wang L, Zhang Y, Schmidt C, Bailer J A, Somia N V, Bogdanove A J, Voytas D F and Plant Biotechnol J. 2012 May; 10(4):373-89. Genome modifications in plant cells by custom-made restriction enzymes. Tzfira T, Weinthal D, Marton I, Zeevi V, Zuker A, Vainstein A.). Genetically-altered semi-determinate Solanaceae plants produced by a method described herein are also claimed.

Alternatively, a method of producing a semi-determinate Solanaceae plant comprises: (a) reducing (partially or completely) function of a wild-type SSP1 gene comprising SEQ ID NO: 1 in a Solanaceae plant homozygous for a mutant sp gene, thereby producing a semi-determinate Solanaceae plant. In some embodiments, reducing the function of the wild-type SSP1 gene comprising SEQ ID NO: 1 comprises performing any of the following methods of RNA-interference (e.g., administering to the Solanaceae plant a micro-RNA or a small interfering (si)-RNA or hairpin RNA) or translational blocking (e.g., administering to the Solanaceae plant a morpholino). Methods of RNA-interference and translational blocking are well-known in the art. Methods of producing micro-RNAs, si-RNAs, and morpholinos are well-known in the art and can involve use of the nucleotides sequences provided herein, e.g., SEQ ID NO: 1. The mutant sp gene can be any mutant sp gene described herein.

EXAMPLES

Identifying Mutant Plants Providing Semi-Determinate Shoot Architecture Phenotypes The crop plant tomato (*Solanum lycopersicum*) was used to identify mutant plants with a semi-determinate phenotype. The previously generated tomato EMS mutation library in the determinate M82 background was used in the methods described below (Menda N Y et al. 2004. Plant J 38.861-72). The mutation library was previously generated by treating seeds with ethyl methanesulfonate (0.5 percent EMS for 12 h; LD15), producing an M1 generation. These seeds were self-crossed to produce 13,000 M2 families with random mutations in unknown locations.

The M82 determinate (M82D) isogenic background is known to contain a mutation in the SELF PRUNING (SP) gene (Pnueli, et al. Development 1989), resulting in a tomato plant with a determinate (D) growth habit. In D-type plants, the sympodial shoots produce progressively fewer leaves until the plant terminates growth in two successive inflorescences. In contrast, indeterminate (ID) tomato plants generate successive sympodial units (SYM) that produce three leaves each, and SYMs continue to reiterate to generate an ID shoot. The M2 EMS mutation library described above was generated in an M82D background and self-crossed to produce approximately six thousand independent mutant tomato plants and many fertile mutants which contained mutations at unidentified locations which were carried over into the M3 inbred generation. These lines were screened in both the M2 and M3 generations for homozygous recessive mutant phenotypes that partially suppressed the determinate growth phenotype of the M82D background, resulting in a semi-determinate shoot architecture phenotype. In particular, flowering time, flower production per inflorescence, and shoot architecture were examined. Single lines were identified that contained at least one M3 plant with a semi-determinate phenotype.

Figure 2:
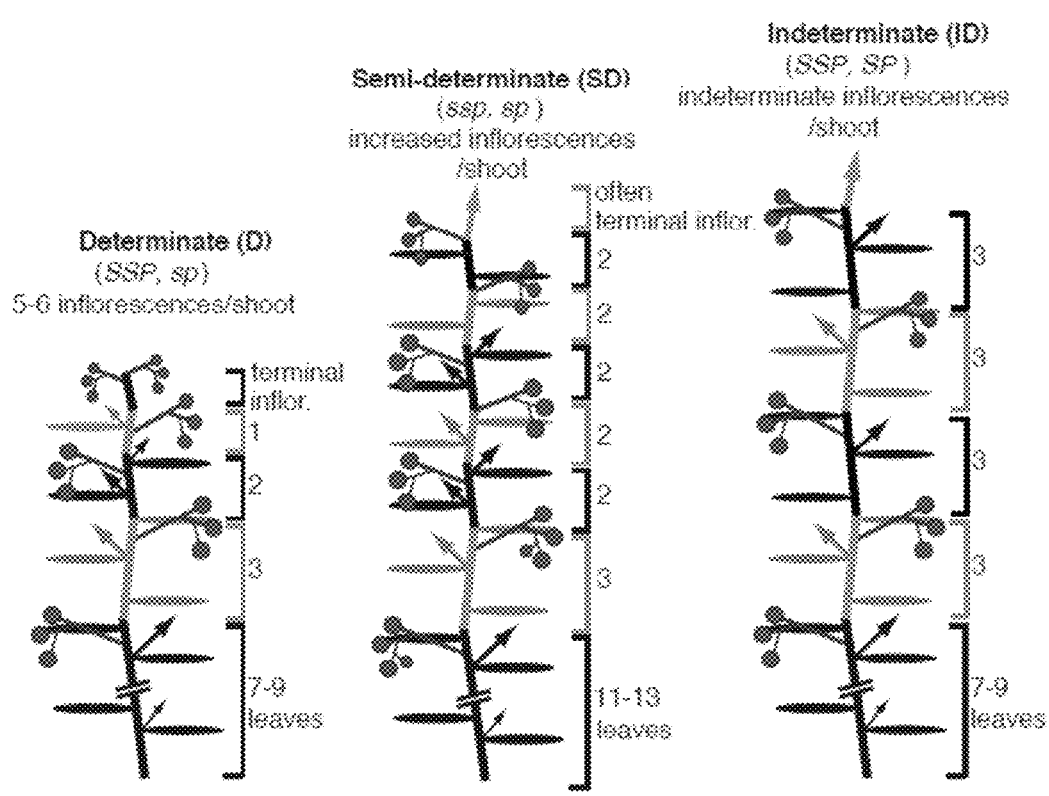
FIG. 2 shows graphical representations of the suppression of sympodial shoot termination in ssp-2129;sp double mutant plants. Left depicts a sp "determinate" (D) mutant plant. Right depicts the wild-type "indeterminate" (ID) tomato plant with fully functional SP and SSP1 genes. Note the three-leaf reiteration of vegetative sympodial shoots (SYM) after the primary shoot produces 7-9 leaves and transitions to flowering. Middle depicts the "semi-determinate" (SD) ssp-2129;sp double mutant plant. Note the reduction in leaf number from three to two in each SYM. Red dots indicate flowers/fruits produced in each inflorescence. Black and gray arrows indicate axillary shoots on the leaf axils.
Figure 3:
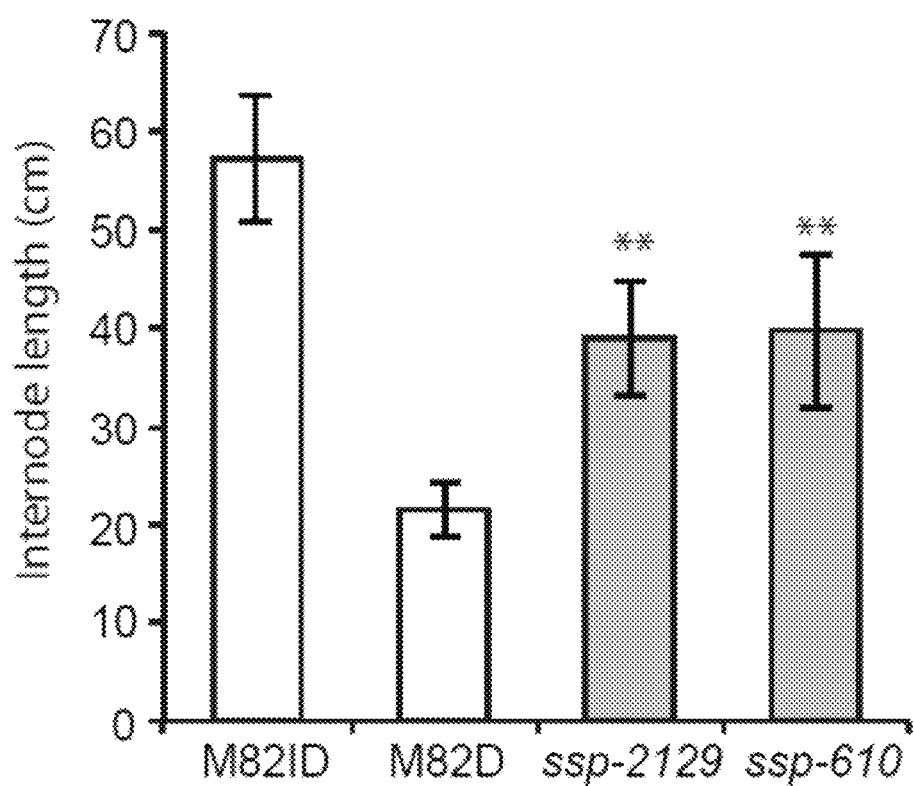
FIG. 3 shows internode length between inflorescences in sympodial units in determinate (M82D), indeterminate (M82ID) and semi-determinate (ssp-2129; sp and ssp-610; sp) plants. Note the intermediate internode length for the semi-determinate ssp-2129; sp double mutant plants.

Two M2 families, e2129 and e610, were identified that had a low frequency (less than or equal to ~25%) of plants with an altered flowering time and shoot architecture resembling a semi-determinate phenotype. FIG. 2 shows that homozygosity for the e2129 mutant (designated ssp-2129) in the $sp^{-/-}$ M82 mutant background suppressed sympodial shoot termination compared to the $sp^{-/-}$ mutant alone. FIG. 2, left, depicts a $sp^{-/-}$ determinate plant where leaf number in each sympodial shoot gradually decreases, leading to shoot termination in two successive inflorescences. FIG. 2, right, depicts an indeterminate wild-type plant where each sympodial unit produces three leaves and this process continues indefinitely. FIG. 2, center, depicts an ssp-2129; $sp^{-/-}$ double mutant with semi-determinate sympodial shoot development, such that each sympodial shoot unit now produces two leaves, instead of the typical three leaves produced in wild-type indeterminate tomato plants. FIG. 3 shows quantification of internode length among 4 inflorescences in determinate $sp^{-/-}$ mutants (M82D), semi-determinate ssp-2129; $sp^{-/-}$ double mutants and ssp-610; $sp^{-/-}$ double mutants (ssp-2129 and ssp-610, respectively), and wild-type plants (M82ID). The p-value was measured by a student's t-test against M82D and M82ID (P<0.01 for ssp-2129 and ssp-610, indicated by **).

Figure 4A:
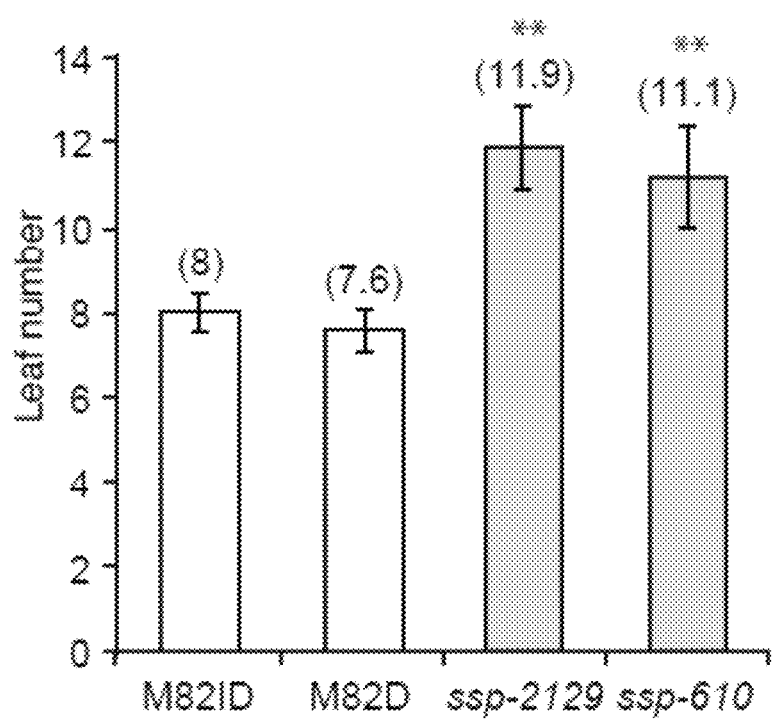
FIGS. 4A to 4C shows shoot meristem determinacy of the primary shoot meristem (PSM), sympodial inflorescence meristem (SIM) and SYM in M82 indeterminate (M82ID), M82 determinate (M82D) and two ssp1 mutant alleles (ssp-2129 and ssp-610).
Figure 4B:
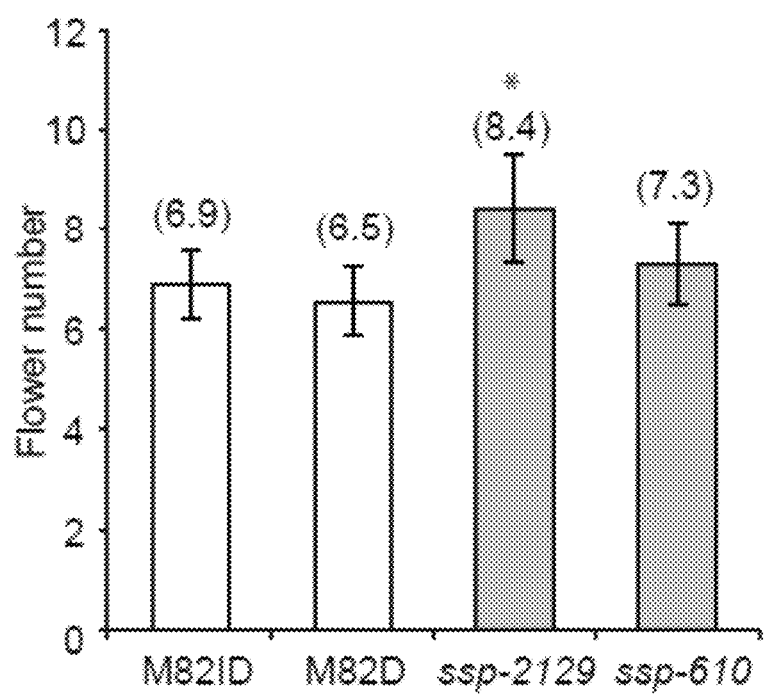
Figure 4C:
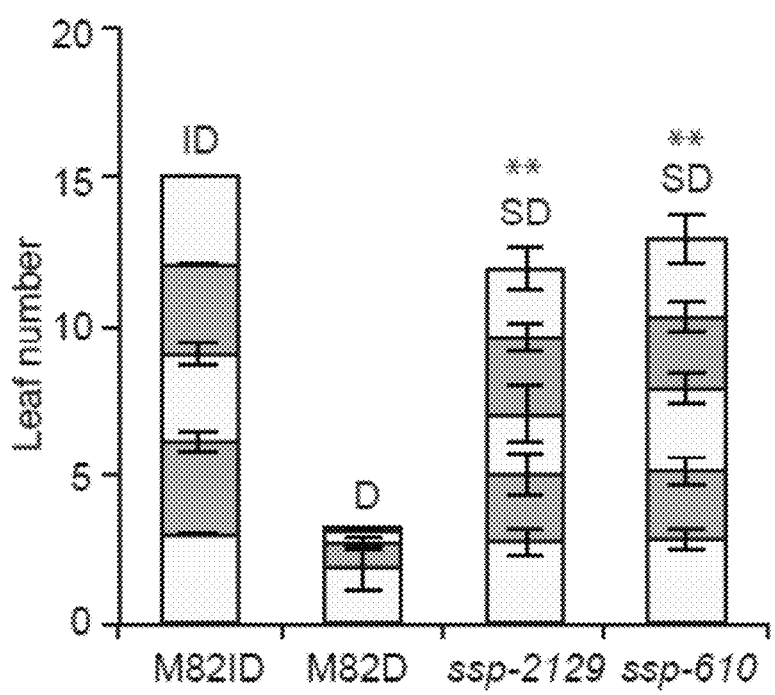

FIG. 4 shows quantification of leaf numbers produced by the primary shoot meristem (PSM) indicating flowering time and sympodial units in both $sp^{-/-}$ and ssp-2129;$sp^{-/-}$ backgrounds. Note that ssp-2129;$sp^{-/-}$ double mutant plants displayed a delayed flowering time as indicated by the increased leaf numbers in the PSM compared to $sp^{-/-}$ single mutant plants. ssp-2129;$sp^{-/-}$ plants also displayed more leaves within sympodial units compared to $sp^{-/-}$ plants, but fewer leaves within sympodial units compared to wild-type indeterminate plants. This semi-determinacy was observed for a second mutant allele, ssp-610 in the sp mutant background.

To identify the genetic mutation(s) resulting in the altered flowering time and shoot architecture in these two families, one family, e2129, was further analyzed using previously reported map-based cloning procedures (Lippman et al, PLoS Biology 2008). A single M3 ssp-2129 mutant plant was crossed to a wild-type species, *S. piminellifolium*, with known polymorphisms throughout the genome (The Tomato Genome sequence, Nature, 2012). The F1 hybrid was then self-crossed to produce an F2 generation of progeny plants segregating for both the ssp-2129 mutation and the DNA polymorphisms between M82 and *S. pimpinellifolium*. Approximately 200 F2 plants were scored for altered flowering time and semi-determinate shoot architecture phenotypes, reflecting homozygosity of the ssp-2129 mutation.

The homozygous mutant F2 plants (those with the altered flowering time and shoot architecture) were then genotyped with evenly spaced polymorphic DNA markers spanning all 12 tomato chromosomes using the bulk segregant mapping technique. DNA was isolated from at least 20 mutant plants (those with the altered flowering time and shoot architecture phenotype) and from 20 wild-type plants. DNA from the mutant plants was pooled to form pool 1 and DNA from the wild-type plants was pooled to form pool 2. A 10 centiMorgan (cM) scan was performed to identify M82 polymorphisms that were over-represented in pool 1 relative to pool 2, reflective of the origin of the ssp-2129 mutation in the M82 background. Over-representation of polymorphisms in pool 1 was found within at 2 Mb mapping interval between PCR markers 4029 and 4230, corresponding to 40M and 42M on chromosome 2, as shown in FIG. 5.

To find the location of the mutation within this region, RNA was extracted from wild-type and mutant plants. This RNA was converted to cDNA and sequenced using Illumina sequencing. The sequencing reads were then mapped to the known gene annotations and only those within the 2 Mb region described above were analyzed. A large number of C to T mutations were observed at a single location, position 647 according to SEQ ID NO: 2 which corresponds to amino acid position 216 according to SEQ ID NO: 5, within the C-terminus of the tomato orthologue of the *Arabidopsis* FLOWERING LOCUS D (FD) gene. The tomato orthologue is referred herein as SUPPRESSOR OF SP1 (SSP1).

Following identification of the mutation present in the e2129 family, the e610 mutant, a confirmed allele in the SSP1 gene by complementation test with the ssp-2129 mutant as described below, was examined to see if the unknown mutation in that family also occurred in the SSP1 gene. Heterozygous plants with one copy of ssp-2129 and one copy of ssp-610 phenocopied the ssp-2129 homozygous mutant and the ssp-610 homozygous mutant plant, indicating that these two mutations were in the same gene. Following the complementation test, DNA was extracted from e610 mutant plants and Sanger sequencing was performed to determine if the SSP1 gene locus contained a mutation. An 'C' to 'T' mutation was identified in SSP1 at position 641 according to SEQ ID NO: 3 which corresponds to amino acid position 214 according to SEQ ID NO: 6.

Figure 5:
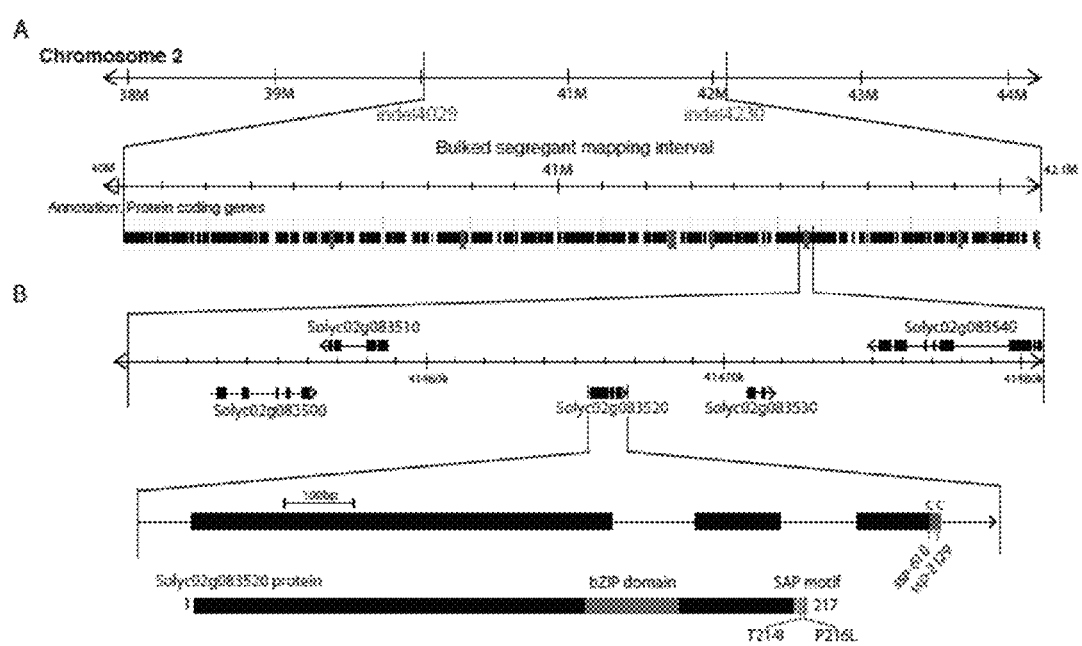
FIG. 5 is a schematic of the map-based cloning procedure used to identify the SSP1 gene, which encodes the orthologue of the *Arabidopsis thaliana* FD gene. The highlighted region is the mapping interval identified using map-based cloning. Red bars indicate single nucleotide polymorphisms (SNPs). The green bars are the coding region of SSP1. The C to T mutations in the C terminus of ssp-2129 and ssp-610 are indicated.

FIG. 5 summarizes the map-based cloning of the SSP1 gene discussed above. FIG. 5A shows the SSP1 map position on chromosome 2 localized to a 2.1M interval between markers indel4029 (4029×10 k) and indel4230 (4230×20 k) was defined by bulk segragant analysis. An F2 mapping population segregating for the recessive ssp1 mutant was generated by self-pollinating an *S. pimpinellifolium* sp-x ssp1 sp-(cv. M82) F1 plant. At least four insertion-deletion (indel) PCR markers were used for each of the 12 tomato chromosomes on a pool of DNA composed of 20 ssp1 mutant individuals compared to a pool of DNA composed of 20 wild-type individuals. Deconvolution of the mutant pool revealed a recombination-defined internal of 40M-42.1M on chromosome 2. FIG. 5B depicts Illumina RNA-sequencing (RNA-seq), which was performed on RNA isolated from reproductive meristems and used to identify and reconstruct DNA protein coding sequences from expressed genes in the mapping interval. RNA-seq reads revealed eight genes (red bar) expressed in meristems. Single nucleotide polymorphisms (SNP) were identified relative to the reference annotation for the eight expressed genes, which revealed a C-to-T DNA change in the coding sequence of Solyc02g083520 of the ssp-2129 mutant allele. Sequencing of the ssp-610 allele revealed a C-to-T change at a nearby location in the coding sequence of Solyc02g083520. Each mutation causes a missense amino acid changes in the conserved SAP motif of the closest tomato homolog of the *Arabidopsis* flowering gene FLOWERING LOCUS D (FD), encoding a bZIP transcription factor. Green bar, bZIP domain; blue bar, SAP motif; red bar, mutation sites.

A summary of the sequences of both the wild-type SSP1 gene and the two mutant alleles, ssp-2129 and ssp-610, is provided in FIGS. 6 and 7, which depict ClustalW analyses of the nucleotide and amino acids, respectively. The nucleotide and amino acid sequences for wild-type SSP1, mutant ssp-2129, mutant ssp-610, wild-type SP, and mutant sp are also listed below. Mutations present in the nucleotide and amino acid sequences of each mutant nucleic acid or protein are indicated as underlined and bolded nucleotides or amino acids.

```
Nucleic Acid
>SSP1
                                                           (SEQ ID NO: 1)
ATGTGGTCATCAAGCAGTGATAACAGGGGACTCTCTGCTTCTTCTTCTTCATCTTCATCC

TCATCTCATTCACCATTTTCTCCAAGACTCAAAACAATGGAAGAAGTGTGGAAAGATATT

AATCTTTCTTCACTTCAAGATCACACTACGAATTACTCTAGAGATCATCATCATCTTCAT

GATCATAATCATCAAGCTGCTAATTTTGGTGGAATGATTTTACAAGATTTTTTGGCAAGG

CCTTTTGCTAATGAATCTTCACCAGCAGCAGCAGCAGCAGCAGCCTCCCCTGTTTCAGCT

ACAACTATGCTGAATTTGAACTCTGTTCCTGAGCTTCATTTCTTTGATAACCCATTGAGG

CAAAACTCAATCTTGCACCAACCAAATGCAAGTGGAAGAAAAAGGGTTGTCCCTGAAACA

GAAGACAATTCTACAGGGGATAGAAGAAATCAGAGGATGATCAAGAACAGAGAGTCTGCT

GCTAGATCAAGAGCTAGAAAGCAGGCTTATATGAACGAGTTGGAATCAGAAGTGGCACAT

TTAGTTGAAGAAAATGCAAGGCTCAAGAAGCAGCAGCAACAGTTACGAGTAGATGCAGCT

AATCAAGTTCCCAAAAAGAACACTCTTTATCGGACGTCAACTGCTCCATTTTGA

>ssp-2129
                                                           (SEQ ID NO: 2)
ATGTGGTCATCAAGCAGTGATAACAGGGGACTCTCTGCTTCTTCTTCTTCATCTTCATCC

TCATCTCATTCACCATTTTCTCCAAGACTCAAAACAATGGAAGAAGTGTGGAAAGATATT

AATCTTTCTTCACTTCAAGATCACACTACGAATTACTCTAGAGATCATCATCATCTTCAT

GATCATAATCATCAAGCTGCTAATTTTGGTGGAATGATTTTACAAGATTTTTTGGCAAGG

CCTTTTGCTAATGAATCTTCACCAGCAGCAGCAGCAGCAGCAGCCTCCCCTGTTTCAGCT

ACAACTATGCTGAATTTGAACTCTGTTCCTGAGCTTCATTTCTTTGATAACCCATTGAGG

CAAAACTCAATCTTGCACCAACCAAATGCAAGTGGAAGAAAAAGGGTTGTCCCTGAAACA

GAAGACAATTCTACAGGGGATAGAAGAAATCAGAGGATGATCAAGAACAGAGAGTCTGCT

GCTAGATCAAGAGCTAGAAAGCAGGCTTATATGAACGAGTTGGAATCAGAAGTGGCACAT

TTAGTTGAAGAAAATGCAAGGCTCAAGAAGCAGCAGCAACAGTTACGAGTAGATGCAGCT

AATCAAGTTCCCAAAAAGAACACTCTTTATCGGACGTCAACTGCTCTATTTTGA

>ssp-610
                                                           (SEQ ID NO: 3)
ATGTGGTCATCAAGCAGTGATAACAGGGGACTCTCTGCTTCTTCTTCTTCATCTTCATCC

TCATCTCATTCACCATTTTCTCCAAGACTCAAAACAATGGAAGAAGTGTGGAAAGATATT

AATCTTTCTTCACTTCAAGATCACACTACGAATTACTCTAGAGATCATCATCATCTTCAT

GATCATAATCATCAAGCTGCTAATTTTGGTGGAATGATTTTACAAGATTTTTTGGCAAGG

CCTTTTGCTAATGAATCTTCACCAGCAGCAGCAGCAGCAGCAGCCTCCCCTGTTTCAGCT

ACAACTATGCTGAATTTGAACTCTGTTCCTGAGCTTCATTTCTTTGATAACCCATTGAGG

CAAAACTCAATCTTGCACCAACCAAATGCAAGTGGAAGAAAAAGGGTTGTCCCTGAAACA

GAAGACAATTCTACAGGGGATAGAAGAAATCAGAGGATGATCAAGAACAGAGAGTCTGCT
```

```
GCTAGATCAAGAGCTAGAAAGCAGGCTTATATGAACGAGTTGGAATCAGAAGTGGCACAT

TTAGTTGAAGAAAATGCAAGGCTCAAGAAGCAGCAGCAACAGTTACGAGTAGATGCAGCT

AATCAAGTTCCCAAAAAGAACACTCTTTATCGGACGTCAATGCTCCATTTTGA

Protein
>SSP
                                                          (SEQ ID NO: 4)
MWSSSSDNRGLSASSSSSSSSSSHSPFSPRLKTMEEVWKDINLSSLQDHTTNYSRDHHHLH

DHNHQAANFGGMILQDFLARPFANESSPAAAAAAASPVSATTMLNLNSVPELHFFDNPLR

QNSILHQPNASGRKRVVPETEDNSTGDRRNQRMIKNRESAARSRARKQAYMNELESEVAH

LVEENARLKKQQQQLRVDAANQVPKKNTLYRTSTAPF*

>ssp-2129
                                                          (SEQ ID NO: 5)
MWSSSSDNRGLSASSSSSSSSSSHSPFSPRLKTMEEVWKDINLSSLQDHTTNYSRDHHHLH

DHNHQAANFGGMILQDFLARPFANESSPAAAAAAASPVSATTMLNLNSVPELHFFDNPLR

QNSILHQPNASGRKRVVPETEDNSTGDRRNQRMIKNRESAARSRARKQAYMNELESEVAH

LVEENARLKKQQQQLRVDAANQVPKKNTLYRTSTALF*

>ssp-610
                                                          (SEQ ID NO: 6)
MWSSSSDNRGLSASSSSSSSSSSHSPFSPRLKTMEEVWKDINLSSLQDHTTNYSRDHHHLH

DHNHQAANFGGMILQDFLARPFANESSPAAAAAAASPVSATTMLNLNSVPELHFFDNPLR

QNSILHQPNASGRKRVVPETEDNSTGDRRNQRMIKNRESAARSRARKQAYMNELESEVAH

LVEENARLKKQQQQLRVDAANQVPKKNTLYRTSIAPF*

Nucleic acid
>SP (wild-type)
                                                          (SEQ ID NO: 7)
ATGGCTTCCAAAATGTGTGAACCCCTTGTGATTGGTAGAGTGATTGGTGAAGTTGTTGATTATTCT

GTCCAAGTGTTAAGATGTCTGTTGTTTATAACAACAACAAACATGTCTATAATGGACATGAATTCT

TTCCTTCCTCAGTAACTTCTAAACCTAGGGTTGAAGTTCATGGTGGTGATCTCAGATCCTTCTTCAC

ACTGATCATGATAGATCCAGATGTTCCTGGTCCTAGTGATCCATATCTCAGGGAACATCTACACTG

GATTGTCACAGACATTCCAGGCACTACAGATTGCTCTTTTGGAAGAGAAGTGGTTGGGTATGAAAT

GCCAAGGCCAAATATTGGAATCCACAGGTTTGTATTTTTGCTGTTTAAGCAGAAGAAAAGGCAAA

CAATATCGAGTGCACCAGTGTCCAGAGATCAATTTAGTAGTAGAAAATTTTCAGAAGAAAATGAA

CTTGGCTCACCAGTTGCTGCTGTTTTCTTCAATTGTCAGAGGGAAACTGCCGCTAGAAGGCGTTGA

>sp (mutant)
                                                          (SEQ ID NO: 8)
ATGGCTTCCAAAATGTGTGAACCCCTTGTGATTGGTAGAGTGATTGGTGAAGTTGTTGATTATTCT

GTCCAAGTGTTAAGATGTCTGTTGTTTATAACAACAACAAACATGTCTATAATGGACATGAATTCT

TTCCTTCCTCAGTAACTTCTAAACCTAGGGTTGAAGTTCATGGTGGTGATCTCAGATCCTTCTTCAC

ACTGATCATGATAGATCCAGATGTTCTTGGTCCTAGTGATCCATATCTCAGGGAACATCTACACTG

GATTGTCACAGACATTCCAGGCACTACAGATTGCTCTTTTGGAAGAGAAGTGGTTGGGTATGAAAT

GCCAAGGCCAAATATTGGAATCCACAGGTTTGTATTTTTGCTGTTTAAGCAGAAGAAAAGGCAAA

CAATATCGAGTGCACCAGTGTCCAGAGATCAATTTAGTAGTAGAAAATTTTCAGAAGAAAATGAA

CTTGGCTCACCAGTTGCTGCTGTTTTCTTCAATTGTCAGAGGGAAACTGCCGCTAGAAGGCGTTGA

Protein
>SP (wild-type)
                                                          (SEQ ID NO: 9)
MASKMCEPLVIGRVIGEVVDYFCPSVI(MSVVYNNNKHVYNGHEFFPSSVISKPRVEVHGG

DLRSEFTLIMIDPDVPGPSDPYLREHLHWIVTDIPGTTDCSFGREVVGYEMPRPNIGIHR
```

-continued

FVFLLFKQKKRQTISSAPVSRDQESSRKFSEENELGSPVAAVFFNCQRETAARRR*

>sp (mutant)

(SEQ ID NO: 10)

MASKMCEPLVIGRVIGEVVDYFCPSVI(MSVVYNNNKHVYNGHEFFPSSVISKPRVEVHGG

DLRSEFTLIMIDPDVLGPSDPYLREHLHWIVTDIPGTTDCSFGREVVGYEMPRPNIGIHR

FVFLLFKQKKRQTISSAPVSRDQFSSRKFSEENELGSPVAAVFFNCQRETAARRR*

Without further elaboration, it is believed that one skilled in the art can, based on the above description, utilize the present disclosure to its fullest extent. The specific embodiments are, therefore, to be construed as merely illustrative, and not limitative of the remainder of the disclosure in any way whatsoever. All publications cited herein are incorporated by reference for the purposes or subject matter referenced herein.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

What is claimed is:

1. A genetically-altered semi-determinate tomato plant homozygous for a mutant suppressor of sp1 (ssp1) gene that encodes a mutant ssp1 protein that comprises a mutant SAP motif and homozygous for a mutant self pruning (sp) gene.

2. A genetically-altered semi-determinate tomato plant homozygous for a mutant ssp1 gene that encodes a mutant ssp1 protein that comprises a mutant SAP motif and homozygous for a mutant sp gene, wherein the mutant ssp1 gene comprises a nucleic acid sequence that encodes a mutant ssp1 protein that comprises a mutant SAP motif that comprises the sequence of SEQ ID NO: 14 or SEQ ID NO: 15.

3. A genetically-altered semi-determinate tomato plant homozygous for a mutant ssp1 gene that encodes a mutant ssp1 polypeptide comprising the sequence of SEQ ID NO: 5 or SEQ ID NO: 6; homozygous for a mutant ssp1 gene that comprises a C to T mutation at position 641 of SEQ ID NO: 1, a C to T mutation at position 647 of SEQ ID NO: 1 or a C to T mutation at position 641 and position 647 of SEQ ID NO: 1; or homozygous for a mutant ssp1 gene that comprises the nucleic acid sequence of SEQ ID NO: 2 or SEQ ID NO: 3.

4. The genetically-altered semi-determinate tomato plant of claim 3, wherein the mutant sp gene comprises the nucleic acid sequence of SEQ ID NO: 8.

5. The genetically-altered semi-determinate tomato plant of claim 1, wherein the genetically-altered semi-determinate tomato plant is isogenic.

6. The genetically-altered semi-determinate tomato plant of claim 1, wherein the genetically-altered semi-determinate tomato plant is inbred.

7. A seed for producing a genetically-altered semi-determinate tomato plant of claim 1.

8. A method of producing a genetically-altered semi-determinate tomato plant comprising:
 (a) genetically altering a ssp1 gene in a tomato-plant containing a mutant sp gene, thereby producing a genetically-altered tomato plant containing a mutant ssp1 gene that encodes a mutant ssp1 protein that comprises a mutant SAP motif and a mutant sp gene; and
 (b) self-crossing the genetically-altered tomato plant produced in (a) or crossing two genetically-altered tomato plants produced in (a) under conditions appropriate for producing a genetically-altered tomato plant homozygous for the mutant ssp1 gene that encodes a mutant ssp1 protein that comprises a mutant SAP motif and homozygous for the mutant sp gene, thereby producing a genetically-altered tomato plant that is semi-determinate.

9. A method of producing a genetically-altered semi-determinate tomato plant comprising:
 (a) producing a genetically-altered tomato plant part containing a mutant ssp1 gene that encodes a mutant ssp1 protein that comprises a mutant SAP motif and a mutant sp gene;
 (b) maintaining the genetically-altered tomato plant part containing a mutant ssp1 and a mutant sp gene produced in (a) under conditions and for sufficient time for production of a genetically-altered tomato plant containing the mutant ssp1 gene and the mutant sp gene from the plant part, thereby producing a genetically-altered tomato plant containing the mutant ssp1 gene and the mutant sp gene;
 (c) self-crossing the genetically-altered tomato plant produced in (b) or crossing two genetically-altered tomato plants produced in (b) under conditions appropriate for producing a genetically-altered tomato plant homozygous for the mutant ssp1 gene and the mutant sp gene, thereby producing a genetically-altered tomato plant that is semi-determinate.

10. A method of producing a genetically-altered semi-determinate tomato plant comprising:
 (a) producing a genetically-altered tomato plant containing a mutant ssp1 gene that encodes a mutant ssp1 protein that comprises a mutant SAP motif and a mutant sp gene; and
 (b) self-crossing the genetically-altered tomato plant produced in (a) or crossing two genetically-altered tomato plants produced in (a) under conditions appropriate for producing a genetically-altered tomato plant homozygous for the mutant ssp1 gene that encodes a mutant ssp1 protein that comprises a mutant SAP motif and homozygous for the mutant sp gene, thereby producing a genetically-altered tomato plant that is semi-determinate, wherein the mutant ssp1 gene comprises a nucleic acid sequence that encodes a mutant ssp1 protein that comprises a mutant SAP motif with a sequence of SEQ ID NO: 14 or SEQ ID NO: 15.

11. A method of producing a genetically-altered semi-determinate tomato plant comprising:
 (a) producing a genetically-altered tomato plant containing a mutant ssp1 gene that encodes a mutant ssp1 protein that comprises a mutant SAP motif and a mutant sp gene; and
 (b) self-crossing the genetically-altered tomato plant produced in (a) or crossing two genetically-altered tomato plants produced in (a) under conditions appropriate for producing a genetically-altered tomato plant homozygous for the mutant ssp1 gene that encodes a mutant ssp1 protein that comprises a mutant SAP motif and homozygous for the mutant sp gene, thereby producing a genetically-altered tomato plant that is semi-determinate, wherein the mutant ssp1 gene encodes a mutant ssp1 polypeptide comprising the sequence of SEQ ID NO: 5 or SEQ ID NO: 6.

12. A method of producing a genetically-altered semi-determinate tomato plant comprising:
 (a) producing a genetically-altered tomato plant containing a mutant ssp1 gene that encodes a mutant ssp1 protein that comprises a mutant SAP motif and a mutant sp gene; and
 (b) self-crossing the genetically-altered tomato plant produced in (a) or crossing two genetically-altered tomato plants produced in (a) under conditions appropriate for producing a genetically-altered tomato plant homozygous for the mutant ssp1 gene that encodes a mutant ssp1 protein that comprises a mutant SAP motif and homozygous for the mutant sp gene, thereby producing a genetically-altered tomato plant that is semi-determinate, wherein the mutant ssp1 gene comprises a C to T mutation at position 641 of SEQ ID NO: 1, a C to T mutation at position 647 of SEQ ID NO: 1, or a C to T mutation at position 641 and 647 of SEQ ID NO: 1.

13. A method of producing a genetically-altered semi-determinate tomato plant comprising:
 (a) producing a genetically-altered tomato plant containing a mutant ssp1 gene that encodes a mutant ssp1 protein that comprises a mutant SAP motif and a mutant sp gene; and
 (b) self-crossing the genetically-altered tomato plant produced in (a) or crossing two genetically-altered tomato plants produced in (a) under conditions appropriate for producing a genetically-altered tomato plant homozygous for the mutant ssp1 gene that encodes a mutant ssp1 protein that comprises a mutant SAP motif and homozygous for the mutant sp gene, thereby producing a genetically-altered tomato plant that is semi-determinate, wherein the mutant ssp1 gene comprises the nucleic acid sequence of SEQ ID NO: 2 or SEQ ID NO: 3.

14. The method of claim 10, wherein the mutant sp gene comprises the nucleic acid sequence of SEQ ID NO: 8.

15. The method of claim 8, wherein the tomato plant is inbred.

\* \* \* \* \*

UNITED STATES PATENT AND TRADEMARK OFFICE
CERTIFICATE OF CORRECTION

PATENT NO. : 9,732,352 B2
APPLICATION NO. : 13/799831
DATED : August 15, 2017
INVENTOR(S) : Zachary Lippman et al.

It is certified that error appears in the above-identified patent and that said Letters Patent is hereby corrected as shown below:

In the Claims

At Column 37, in Line 8, the claim should be amended as indicated below:
(a) genetically altering a ssp1 gene in a tomato_plant Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 21

<210> SEQ ID NO 1
<211> LENGTH: 654
<212> TYPE: DNA
<213> ORGANISM: S. lycopersicum

<400> SEQUENCE: 1
atgtggtcat caagcagtga taacagggga ctctctgctt cttcttcttc atcttcatcc      60
tcatctcatt caccattttc tccaagactc aaaacaatgg aagaagtgtg gaaagatatt     120
aatctttctt cacttcaaga tcacactacg aattactcta gagatcatca tcatcttcat     180
gatcataatc atcaagctgc taattttggt ggaatgattt tacaagattt tttggcaagg     240
ccttttgcta atgaatcttc accagcagca gcagcagcag cagcctcccc tgtttcagct     300
acaactatgc tgaatttgaa ctctgttcct gagcttcatt tctttgataa cccattgagg     360
caaaactcaa tcttgcacca accaaatgca agtggaagaa aagggttgt ccctgaaaca      420 gaagacaatt ctacagggga tagaagaaat cagaggatga tcaagaacag agagtctgct    480
gctagatcaa gagctagaaa gcaggcttat atgaacgagt tggaatcaga agtggcacat    540
ttagttgaag aaaatgcaag gctcaagaag cagcagcaac agttacgagt agatgcagct    600
aatcaagttc ccaaaaagaa cactctttat cggacgtcaa ctgctccatt ttga           654

<210> SEQ ID NO 2
<211> LENGTH: 654
<212> TYPE: DNA
<213> ORGANISM: S. lycopersicum

<400> SEQUENCE: 2
atgtggtcat caagcagtga taacagggga ctctctgctt cttcttcttc atcttcatcc      60
tcatctcatt caccattttc tccaagactc aaaacaatgg aagaagtgtg gaaagatatt     120
aatctttctt cacttcaaga tcacactacg aattactcta gagatcatca tcatcttcat     180
gatcataatc atcaagctgc taattttggt ggaatgattt tacaagattt tttggcaagg     240
ccttttgcta atgaatcttc accagcagca gcagcagcag cagcctcccc tgtttcagct     300
acaactatgc tgaatttgaa ctctgttcct gagcttcatt tctttgataa cccattgagg     360
caaaactcaa tcttgcacca accaaatgca agtggaagaa aagggttgt ccctgaaaca      420 gaagacaatt ctacagggga tagaagaaat cagaggatga tcaagaacag agagtctgct    480
```

```
gctagatcaa gagctagaaa gcaggcttat atgaacgagt tggaatcaga agtggcacat    540
ttagttgaag aaaatgcaag gctcaagaag cagcagcaac agttacgagt agatgcagct    600
aatcaagttc ccaaaaagaa cactctttat cggacgtcaa ctgctctatt ttga          654
```

<210> SEQ ID NO 3
<211> LENGTH: 654
<212> TYPE: DNA
<213> ORGANISM: S. lycopersicum

<400> SEQUENCE: 3

```
atgtggtcat caagcagtga taacagggga ctctctgctt cttcttcttc atcttcatcc     60
tcatctcatt caccattttc tccaagactc aaaacaatgg aagaagtgtg aaagatatt    120 aatctttctt cacttcaaga tcacactacg aattactcta gagatcatca tcatcttcat   180
gatcataatc atcaagctgc taattttggt ggaatgattt tacaagattt tttggcaagg   240
ccttttgcta atgaatcttc accagcagca gcagcagcag cagcctcccc tgtttcagct   300
acaactatgc tgaatttgaa ctctgttcct gagcttcatt tctttgataa cccattgagg   360
caaaactcaa tcttgcacca accaaatgca agtggaagaa aagggttgt ccctgaaaca    420 gaagacaatt ctacagggga tagaagaaat cagaggatga tcaagaacag agagtctgct   480
gctagatcaa gagctagaaa gcaggcttat atgaacgagt tggaatcaga agtggcacat   540
ttagttgaag aaaatgcaag gctcaagaag cagcagcaac agttacgagt agatgcagct   600
aatcaagttc ccaaaaagaa cactctttat cggacgtcaa ttgctccatt ttga          654
```

<210> SEQ ID NO 4
<211> LENGTH: 217
<212> TYPE: PRT
<213> ORGANISM: S. lycopersicum

<400> SEQUENCE: 4

```
Met Trp Ser Ser Ser Asp Asn Arg Gly Leu Ser Ala Ser Ser Ser
1               5                   10                  15

Ser Ser Ser Ser Ser Ser His Ser Pro Phe Ser Pro Arg Leu Lys Thr
            20                  25                  30

Met Glu Glu Val Trp Lys Asp Ile Asn Leu Ser Ser Leu Gln Asp His
        35                  40                  45

Thr Thr Asn Tyr Ser Arg Asp His His His Leu His Asp His Asn His
    50                  55                  60

Gln Ala Ala Asn Phe Gly Gly Met Ile Leu Gln Asp Phe Leu Ala Arg
65                  70                  75                  80

Pro Phe Ala Asn Glu Ser Ser Pro Ala Ala Ala Ala Ala Ala Ala Ser
                85                  90                  95

Pro Val Ser Ala Thr Thr Met Leu Asn Leu Asn Ser Val Pro Glu Leu
            100                 105                 110

His Phe Phe Asp Asn Pro Leu Arg Gln Asn Ser Ile Leu His Gln Pro
        115                 120                 125

Asn Ala Ser Gly Arg Lys Arg Val Val Pro Glu Thr Glu Asp Asn Ser
    130                 135                 140

Thr Gly Asp Arg Arg Asn Gln Arg Met Ile Lys Asn Arg Glu Ser Ala
145                 150                 155                 160

Ala Arg Ser Arg Ala Arg Lys Gln Ala Tyr Met Asn Glu Leu Glu Ser
                165                 170                 175

Glu Val Ala His Leu Val Glu Glu Asn Ala Arg Leu Lys Lys Gln Gln
            180                 185                 190
```

Gln Gln Leu Arg Val Asp Ala Ala Asn Gln Val Pro Lys Lys Asn Thr
        195                 200                 205

Leu Tyr Arg Thr Ser Thr Ala Pro Phe
        210                 215

<210> SEQ ID NO 5
<211> LENGTH: 217
<212> TYPE: PRT
<213> ORGANISM: S. lycopersicum

<400> SEQUENCE: 5

Met Trp Ser Ser Ser Ser Asp Asn Arg Gly Leu Ser Ala Ser Ser Ser
1               5                   10                  15

Ser Ser Ser Ser Ser Ser His Ser Pro Phe Ser Pro Arg Leu Lys Thr
                20                  25                  30

Met Glu Glu Val Trp Lys Asp Ile Asn Leu Ser Ser Leu Gln Asp His
            35                  40                  45

Thr Thr Asn Tyr Ser Arg Asp His His His Leu His Asp His Asn His
        50                  55                  60

Gln Ala Ala Asn Phe Gly Gly Met Ile Leu Gln Asp Phe Leu Ala Arg
65                  70                  75                  80

Pro Phe Ala Asn Glu Ser Ser Pro Ala Ala Ala Ala Ala Ala Ala Ser
                85                  90                  95

Pro Val Ser Ala Thr Thr Met Leu Asn Leu Asn Ser Val Pro Glu Leu
            100                 105                 110

His Phe Phe Asp Asn Pro Leu Arg Gln Asn Ser Ile Leu His Gln Pro
        115                 120                 125

Asn Ala Ser Gly Arg Lys Arg Val Val Pro Glu Thr Glu Asp Asn Ser
    130                 135                 140

Thr Gly Asp Arg Arg Asn Gln Arg Met Ile Lys Asn Arg Glu Ser Ala
145                 150                 155                 160

Ala Arg Ser Arg Ala Arg Lys Gln Ala Tyr Met Asn Glu Leu Glu Ser
                165                 170                 175

Glu Val Ala His Leu Val Glu Glu Asn Ala Arg Leu Lys Lys Gln Gln
            180                 185                 190

Gln Gln Leu Arg Val Asp Ala Ala Asn Gln Val Pro Lys Lys Asn Thr
        195                 200                 205

Leu Tyr Arg Thr Ser Thr Ala Leu Phe
        210                 215

<210> SEQ ID NO 6
<211> LENGTH: 217
<212> TYPE: PRT
<213> ORGANISM: S. lycopersicum

<400> SEQUENCE: 6

Met Trp Ser Ser Ser Ser Asp Asn Arg Gly Leu Ser Ala Ser Ser Ser
1               5                   10                  15

Ser Ser Ser Ser Ser Ser His Ser Pro Phe Ser Pro Arg Leu Lys Thr
                20                  25                  30

Met Glu Glu Val Trp Lys Asp Ile Asn Leu Ser Ser Leu Gln Asp His
            35                  40                  45

Thr Thr Asn Tyr Ser Arg Asp His His His Leu His Asp His Asn His
        50                  55                  60

Gln Ala Ala Asn Phe Gly Gly Met Ile Leu Gln Asp Phe Leu Ala Arg
65                  70                  75                  80

```
Pro Phe Ala Asn Glu Ser Ser Pro Ala Ala Ala Ala Ala Ser
            85                  90                  95

Pro Val Ser Ala Thr Thr Met Leu Asn Leu Asn Ser Val Pro Glu Leu
            100                 105                 110

His Phe Phe Asp Asn Pro Leu Arg Gln Asn Ser Ile Leu His Gln Pro
            115                 120                 125

Asn Ala Ser Gly Arg Lys Arg Val Val Pro Glu Thr Glu Asp Asn Ser
            130                 135                 140

Thr Gly Asp Arg Arg Asn Gln Arg Met Ile Lys Asn Arg Glu Ser Ala
145                 150                 155                 160

Ala Arg Ser Arg Ala Arg Lys Gln Ala Tyr Met Asn Glu Leu Glu Ser
            165                 170                 175

Glu Val Ala His Leu Val Glu Glu Asn Ala Arg Leu Lys Lys Gln Gln
            180                 185                 190

Gln Gln Leu Arg Val Asp Ala Ala Asn Gln Val Pro Lys Lys Asn Thr
            195                 200                 205

Leu Tyr Arg Thr Ser Ile Ala Pro Phe
            210                 215
```

```
<210> SEQ ID NO 7
<211> LENGTH: 528
<212> TYPE: DNA
<213> ORGANISM: S. lycopersicum

<400> SEQUENCE: 7
atggcttcca aaatgtgtga accccttgtg attggtagag tgattggtga agttgttgat        60
tatttctgtc caagtgttaa gatgtctgtt gtttataaca acaacaaaca tgtctataat       120
ggacatgaat tctttccttc ctcagtaact tctaaaccta gggttgaagt tcatggtggt       180
gatctcagat ccttcttcac actgatcatg atagatccag atgttcctgg tcctagtgat       240
ccatatctca gggaacatct acactggatt gtcacagaca ttccaggcac tacagattgc       300
tcttttggaa gagaagtggt tgggtatgaa atgccaaggc caaatattgg aatccacagg       360
tttgtatttt gctgtgttaa gcagaagaaa aggcaaacaa tatcgagtgc accagtgtcc       420
agagatcaat ttagtagtag aaaattttca gaagaaaatg aacttggctc accagttgct       480 gctgtttttct tcaattgtca gagggaaact gccgctagaa ggcgttga                   528

<210> SEQ ID NO 8
<211> LENGTH: 528
<212> TYPE: DNA
<213> ORGANISM: S. lycopersicum

<400> SEQUENCE: 8
atggcttcca aaatgtgtga accccttgtg attggtagag tgattggtga agttgttgat        60
tatttctgtc caagtgttaa gatgtctgtt gtttataaca acaacaaaca tgtctataat       120
ggacatgaat tctttccttc ctcagtaact tctaaaccta gggttgaagt tcatggtggt       180
gatctcagat ccttcttcac actgatcatg atagatccag atgttcttgg tcctagtgat       240
ccatatctca gggaacatct acactggatt gtcacagaca ttccaggcac tacagattgc       300
tcttttggaa gagaagtggt tgggtatgaa atgccaaggc caaatattgg aatccacagg       360
tttgtatttt gctgtgttaa gcagaagaaa aggcaaacaa tatcgagtgc accagtgtcc       420
agagatcaat ttagtagtag aaaattttca gaagaaaatg aacttggctc accagttgct       480 gctgtttttct tcaattgtca gagggaaact gccgctagaa ggcgttga                   528
```

<210> SEQ ID NO 9
<211> LENGTH: 175
<212> TYPE: PRT
<213> ORGANISM: S. lycopersicum

<400> SEQUENCE: 9

```
Met Ala Ser Lys Met Cys Glu Pro Leu Val Ile Gly Arg Val Ile Gly
1               5                   10                  15

Glu Val Val Asp Tyr Phe Cys Pro Ser Val Lys Met Ser Val Val Tyr
            20                  25                  30

Asn Asn Asn Lys His Val Tyr Asn Gly His Glu Phe Phe Pro Ser Ser
        35                  40                  45

Val Thr Ser Lys Pro Arg Val Glu Val His Gly Gly Asp Leu Arg Ser
    50                  55                  60

Phe Phe Thr Leu Ile Met Ile Asp Pro Asp Val Pro Gly Pro Ser Asp
65                  70                  75                  80

Pro Tyr Leu Arg Glu His Leu His Trp Ile Val Thr Asp Ile Pro Gly
                85                  90                  95

Thr Thr Asp Cys Ser Phe Gly Arg Glu Val Val Gly Tyr Glu Met Pro
            100                 105                 110

Arg Pro Asn Ile Gly Ile His Arg Phe Val Phe Leu Leu Phe Lys Gln
        115                 120                 125

Lys Lys Arg Gln Thr Ile Ser Ser Ala Pro Val Ser Arg Asp Gln Phe
    130                 135                 140

Ser Ser Arg Lys Phe Ser Glu Glu Asn Glu Leu Gly Ser Pro Val Ala
145                 150                 155                 160

Ala Val Phe Phe Asn Cys Gln Arg Glu Thr Ala Ala Arg Arg Arg
                165                 170                 175
```

<210> SEQ ID NO 10
<211> LENGTH: 175
<212> TYPE: PRT
<213> ORGANISM: S. lycopersicum

<400> SEQUENCE: 10

```
Met Ala Ser Lys Met Cys Glu Pro Leu Val Ile Gly Arg Val Ile Gly
1               5                   10                  15

Glu Val Val Asp Tyr Phe Cys Pro Ser Val Lys Met Ser Val Val Tyr
            20                  25                  30

Asn Asn Asn Lys His Val Tyr Asn Gly His Glu Phe Phe Pro Ser Ser
        35                  40                  45

Val Thr Ser Lys Pro Arg Val Glu Val His Gly Gly Asp Leu Arg Ser
    50                  55                  60

Phe Phe Thr Leu Ile Met Ile Asp Pro Asp Val Leu Gly Pro Ser Asp
65                  70                  75                  80

Pro Tyr Leu Arg Glu His Leu His Trp Ile Val Thr Asp Ile Pro Gly
                85                  90                  95

Thr Thr Asp Cys Ser Phe Gly Arg Glu Val Val Gly Tyr Glu Met Pro
            100                 105                 110

Arg Pro Asn Ile Gly Ile His Arg Phe Val Phe Leu Leu Phe Lys Gln
        115                 120                 125

Lys Lys Arg Gln Thr Ile Ser Ser Ala Pro Val Ser Arg Asp Gln Phe
    130                 135                 140

Ser Ser Arg Lys Phe Ser Glu Glu Asn Glu Leu Gly Ser Pro Val Ala
145                 150                 155                 160
```

```
Ala Val Phe Phe Asn Cys Gln Arg Glu Thr Ala Ala Arg Arg
            165                 170                 175
```

<210> SEQ ID NO 11
<211> LENGTH: 7
<212> TYPE: PRT
<213> ORGANISM: S. lycopersicum

<400> SEQUENCE: 11

```
Arg Thr Ser Thr Ala Pro Phe
1               5
```

<210> SEQ ID NO 12
<211> LENGTH: 21
<212> TYPE: DNA
<213> ORGANISM: S. lycopersicum

<400> SEQUENCE: 12
cggacgtcaa ctgctctatt t                                           21

<210> SEQ ID NO 13
<211> LENGTH: 21
<212> TYPE: DNA
<213> ORGANISM: S. lycopersicum

<400> SEQUENCE: 13
cggacgtcaa ttgctccatt t                                           21

<210> SEQ ID NO 14
<211> LENGTH: 7
<212> TYPE: PRT
<213> ORGANISM: S. lycopersicum

<400> SEQUENCE: 14

```
Arg Thr Ser Thr Ala Leu Phe
1               5
```

<210> SEQ ID NO 15
<211> LENGTH: 7
<212> TYPE: PRT
<213> ORGANISM: S. lycopersicum

<400> SEQUENCE: 15

```
Arg Thr Ser Ile Ala Pro Phe
1               5
```

<210> SEQ ID NO 16
<211> LENGTH: 654
<212> TYPE: DNA
<213> ORGANISM: S. lycopersicum

<400> SEQUENCE: 16
atgtggtcat caagcagtga taacagggga ctctctgctt cttcttcttc atcttcatcc    60
tcatctcatt caccattttc tccaagactc aaaacaatgg aagaagtgtg gaaagatatt   120
aatctttctt cacttcaaga tcacactacg aattactcta gagatcatca tcatcttcat   180
gatcataatc atcaagctgc taattttggt ggaatgattt tacaagattt tttggcaagg   240
ccttttgcta atgaatcttc accagcagca gcagcagcag cagcctcccc tgtttcagct   300
acaactatgc tgaatttgaa ctctgttcct gagcttcatt tctttgataa cccattgagg   360
caaaactcaa tcttgcacca accaaatgca agtggaagaa aaagggttgt ccctgaaaca   420

-continued

| | |
|---|---|
| gaagacaatt ctacagggga tagaagaaat cagaggatga tcaagaacag agagtctgct | 480 |
| gctagatcaa gagctagaaa gcaggcttat atgaacgagt tggaatcaga agtggcacat | 540 |
| ttagttgaag aaaatgcaag gctcaagaag cagcagcaac agttacgagt agatgcagct | 600 |
| aatcaagttc ccaaaaagaa cactctttat cggacgtcaa ctgctccatt ttga | 654 |

<210> SEQ ID NO 17
<211> LENGTH: 654
<212> TYPE: DNA
<213> ORGANISM: S. lycopersicum

<400> SEQUENCE: 17

| | |
|---|---|
| atgtggtcat caagcagtga taacagggga ctctctgctt cttcttcttc atcttcatcc | 60 |
| tcatctcatt caccattttc tccaagactc aaaacaatgg aagaagtgtg aaaagatatt | 120 |
| aatctttctt cacttcaaga tcacactacg aattactcta gagatcatca tcatcttcat | 180 |
| gatcataatc atcaagctgc taattttggt ggaatgattt tacaagattt tttggcaagg | 240 |
| ccttttgcta atgaatcttc accagcagca gcagcagcag cagcctcccc tgtttcagct | 300 |
| acaactatgc tgaatttgaa ctctgttcct gagcttcatt tctttgataa cccattgagg | 360 |
| caaaactcaa tcttgcacca accaaatgca agtggaagaa aaagggttgt ccctgaaaca | 420 |
| gaagacaatt ctacagggga tagaagaaat cagaggatga tcaagaacag agagtctgct | 480 |
| gctagatcaa gagctagaaa gcaggcttat atgaacgagt tggaatcaga agtggcacat | 540 |
| ttagttgaag aaaatgcaag gctcaagaag cagcagcaac agttacgagt agatgcagct | 600 |
| aatcaagttc ccaaaaagaa cactctttat cggacgtcaa ttgctccatt ttga | 654 |

<210> SEQ ID NO 18
<211> LENGTH: 654
<212> TYPE: DNA
<213> ORGANISM: S. lycopersicum

<400> SEQUENCE: 18

| | |
|---|---|
| atgtggtcat caagcagtga taacagggga ctctctgctt cttcttcttc atcttcatcc | 60 |
| tcatctcatt caccattttc tccaagactc aaaacaatgg aagaagtgtg aaaagatatt | 120 |
| aatctttctt cacttcaaga tcacactacg aattactcta gagatcatca tcatcttcat | 180 |
| gatcataatc atcaagctgc taattttggt ggaatgattt tacaagattt tttggcaagg | 240 |
| ccttttgcta atgaatcttc accagcagca gcagcagcag cagcctcccc tgtttcagct | 300 |
| acaactatgc tgaatttgaa ctctgttcct gagcttcatt tctttgataa cccattgagg | 360 |
| caaaactcaa tcttgcacca accaaatgca agtggaagaa aaagggttgt ccctgaaaca | 420 |
| gaagacaatt ctacagggga tagaagaaat cagaggatga tcaagaacag agagtctgct | 480 |
| gctagatcaa gagctagaaa gcaggcttat atgaacgagt tggaatcaga agtggcacat | 540 |
| ttagttgaag aaaatgcaag gctcaagaag cagcagcaac agttacgagt agatgcagct | 600 |
| aatcaagttc ccaaaaagaa cactctttat cggacgtcaa ctgctctatt ttga | 654 |

<210> SEQ ID NO 19
<211> LENGTH: 217
<212> TYPE: PRT
<213> ORGANISM: S. lycopersicum

<400> SEQUENCE: 19

Met Trp Ser Ser Ser Ser Asp Asn Arg Gly Leu Ser Ala Ser Ser Ser
1               5                   10                  15

```
Ser Ser Ser Ser Ser His Ser Pro Phe Ser Pro Arg Leu Lys Thr
            20                  25                  30

Met Glu Glu Val Trp Lys Asp Ile Asn Leu Ser Leu Gln Asp His
        35                  40                  45

Thr Thr Asn Tyr Ser Arg Asp His His His Leu His Asp His Asn His
    50                  55                  60

Gln Ala Ala Asn Phe Gly Gly Met Ile Leu Gln Asp Phe Leu Ala Arg
65                  70                  75                  80

Pro Phe Ala Asn Glu Ser Ser Pro Ala Ala Ala Ala Ala Ala Ala Ser
                85                  90                  95

Pro Val Ser Ala Thr Thr Met Leu Asn Leu Asn Ser Val Pro Glu Leu
                100                 105                 110

His Phe Phe Asp Asn Pro Leu Arg Gln Asn Ser Ile Leu His Gln Pro
            115                 120                 125

Asn Ala Ser Gly Arg Lys Arg Val Val Pro Glu Thr Glu Asp Asn Ser
        130                 135                 140

Thr Gly Asp Arg Arg Asn Gln Arg Met Ile Lys Asn Arg Glu Ser Ala
145                 150                 155                 160

Ala Arg Ser Arg Ala Arg Lys Gln Ala Tyr Met Asn Glu Leu Glu Ser
                165                 170                 175

Glu Val Ala His Leu Val Glu Glu Asn Ala Arg Leu Lys Lys Gln Gln
            180                 185                 190

Gln Gln Leu Arg Val Asp Ala Ala Asn Gln Val Pro Lys Lys Asn Thr
        195                 200                 205

Leu Tyr Arg Thr Ser Thr Ala Pro Phe
    210                 215

<210> SEQ ID NO 20
<211> LENGTH: 217
<212> TYPE: PRT
<213> ORGANISM: S. lycopersicum

<400> SEQUENCE: 20

Met Trp Ser Ser Ser Ser Asp Asn Arg Gly Leu Ser Ala Ser Ser Ser
1               5                   10                  15

Ser Ser Ser Ser Ser His Ser Pro Phe Ser Pro Arg Leu Lys Thr
            20                  25                  30

Met Glu Glu Val Trp Lys Asp Ile Asn Leu Ser Leu Gln Asp His
        35                  40                  45

Thr Thr Asn Tyr Ser Arg Asp His His His Leu His Asp His Asn His
    50                  55                  60

Gln Ala Ala Asn Phe Gly Gly Met Ile Leu Gln Asp Phe Leu Ala Arg
65                  70                  75                  80

Pro Phe Ala Asn Glu Ser Ser Pro Ala Ala Ala Ala Ala Ala Ala Ser
                85                  90                  95

Pro Val Ser Ala Thr Thr Met Leu Asn Leu Asn Ser Val Pro Glu Leu
                100                 105                 110

His Phe Phe Asp Asn Pro Leu Arg Gln Asn Ser Ile Leu His Gln Pro
            115                 120                 125

Asn Ala Ser Gly Arg Lys Arg Val Val Pro Glu Thr Glu Asp Asn Ser
        130                 135                 140

Thr Gly Asp Arg Arg Asn Gln Arg Met Ile Lys Asn Arg Glu Ser Ala
145                 150                 155                 160

Ala Arg Ser Arg Ala Arg Lys Gln Ala Tyr Met Asn Glu Leu Glu Ser
                165                 170                 175
```

```
Glu Val Ala His Leu Val Glu Glu Asn Ala Arg Leu Lys Lys Gln Gln
            180                 185                 190

Gln Gln Leu Arg Val Asp Ala Ala Asn Gln Val Pro Lys Lys Asn Thr
        195                 200                 205

Leu Tyr Arg Thr Ser Thr Ala Leu Phe
    210                 215

<210> SEQ ID NO 21
<211> LENGTH: 217
<212> TYPE: PRT
<213> ORGANISM: S. lycopersicum

<400> SEQUENCE: 21

Met Trp Ser Ser Ser Asp Asn Arg Gly Leu Ser Ala Ser Ser Ser
1               5                   10                  15

Ser Ser Ser Ser Ser Ser His Ser Pro Phe Ser Pro Arg Leu Lys Thr
                20                  25                  30

Met Glu Glu Val Trp Lys Asp Ile Asn Leu Ser Ser Leu Gln Asp His
            35                  40                  45

Thr Thr Asn Tyr Ser Arg Asp His His His Leu His Asp His Asn His
    50                  55                  60

Gln Ala Ala Asn Phe Gly Gly Met Ile Leu Gln Asp Phe Leu Ala Arg
65                  70                  75                  80

Pro Phe Ala Asn Glu Ser Ser Pro Ala Ala Ala Ala Ala Ala Ala Ser
                85                  90                  95

Pro Val Ser Ala Thr Thr Met Leu Asn Leu Asn Ser Val Pro Glu Leu
                100                 105                 110

His Phe Phe Asp Asn Pro Leu Arg Gln Asn Ser Ile Leu His Gln Pro
            115                 120                 125

Asn Ala Ser Gly Arg Lys Arg Val Val Pro Glu Thr Glu Asp Asn Ser
    130                 135                 140

Thr Gly Asp Arg Arg Asn Gln Arg Met Ile Lys Asn Arg Glu Ser Ala
145                 150                 155                 160

Ala Arg Ser Arg Ala Arg Lys Gln Ala Tyr Met Asn Glu Leu Glu Ser
                165                 170                 175

Glu Val Ala His Leu Val Glu Glu Asn Ala Arg Leu Lys Lys Gln Gln
            180                 185                 190

Gln Gln Leu Arg Val Asp Ala Ala Asn Gln Val Pro Lys Lys Asn Thr
        195                 200                 205

Leu Tyr Arg Thr Ser Ile Ala Pro Phe
    210                 215
```